US011274327B2

(12) United States Patent
Wang et al.

(10) Patent No.: US 11,274,327 B2
(45) Date of Patent: *Mar. 15, 2022

(54) METHODS FOR SYNTHESIZING POOLS OF PROBES

(71) Applicant: Affymetrix, Inc., Carlsbad, CA (US)

(72) Inventors: Yuker Wang, Palo Alto, CA (US);
Keith W. Jones, Sunnyvale, CA (US);
Ronald J. Sapolsky, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/656,002

(22) Filed: Oct. 17, 2019

(65) Prior Publication Data

US 2020/0109427 A1 Apr. 9, 2020

Related U.S. Application Data

(60) Division of application No. 15/148,226, filed on May 6, 2016, now Pat. No. 10,513,722, which is a continuation of application No. 14/272,144, filed on May 7, 2014, now Pat. No. 9,359,640, which is a division of application No. 13/426,589, filed on Mar. 21, 2012, now Pat. No. 8,759,036.

(60) Provisional application No. 61/454,914, filed on Mar. 21, 2011.

(51) Int. Cl.
| | |
|---|---|
| *C12Q 1/6832* | (2018.01) |
| *C12N 15/10* | (2006.01) |
| *C12Q 1/6806* | (2018.01) |
| *C12Q 1/6876* | (2018.01) |
| *C12P 19/34* | (2006.01) |
| *C12P 19/28* | (2006.01) |
| *C12Q 1/6811* | (2018.01) |

(52) U.S. Cl.
CPC .......... *C12P 19/34* (2013.01); *C12N 15/1093* (2013.01); *C12P 19/28* (2013.01); *C12Q 1/6806* (2013.01); *C12Q 1/6811* (2013.01); *C12Q 1/6832* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 5,412,087 A | 5/1995 | McGall et al. | |
| 5,624,827 A | 4/1997 | Rosenblum et al. | |
| 5,866,337 A | 2/1999 | Schon | |
| 5,871,921 A | 2/1999 | Landegren et al. | |
| 5,889,165 A | 3/1999 | Fodor et al. | |
| 5,959,098 A | 9/1999 | Goldberg et al. | |
| 6,027,889 A | 2/2000 | Barany et al. | |
| 6,147,205 A | 11/2000 | McGall et al. | |
| 6,262,216 B1 | 7/2001 | McGall et al. | |
| 6,300,070 B1 | 10/2001 | Boles et al. | |
| 6,310,189 B1 | 10/2001 | Fodor et al. | |
| 6,368,799 B1 | 4/2002 | Chee | |
| 6,428,752 B1 | 8/2002 | Montagu | |
| 6,458,530 B1 | 10/2002 | Morris et al. | |
| 6,506,594 B1 | 1/2003 | Barany et al. | |
| 6,558,928 B1 | 5/2003 | Landegren | |
| 6,713,294 B1 | 3/2004 | Krokan et al. | |
| 6,852,487 B1 | 2/2005 | Barany et al. | |
| 6,858,412 B2 | 2/2005 | Willis et al. | |
| 6,946,251 B2 | 9/2005 | Kurn | |
| 7,208,295 B2 | 4/2007 | Faham et al. | |
| 7,320,860 B2 | 1/2008 | Landegren et al. | |
| 7,351,528 B2 | 4/2008 | Landegren | |
| 7,368,242 B2 | 5/2008 | Miao et al. | |
| 7,510,829 B2 | 3/2009 | Faham et al. | |
| 7,700,323 B2 | 4/2010 | Willis et al. | |
| 7,745,091 B2 | 6/2010 | True | |
| 7,862,999 B2 | 1/2011 | Zheng et al. | |
| 8,759,036 B2 * | 6/2014 | Wang ................. | C12Q 1/6832 435/91.2 |
| 2004/0110213 A1 | 6/2004 | Namsaraev | |
| 2004/0115644 A1 | 6/2004 | Dong | |
| 2006/0019304 A1 | 1/2006 | Hardenbol et al. | |
| 2006/0234264 A1 | 10/2006 | Hardenbol | |
| 2007/0065847 A1 | 3/2007 | Namsaraev et al. | |
| 2007/0087417 A1 | 4/2007 | Namsaraev | |
| 2007/0178479 A1 | 8/2007 | Willis et al. | |
| 2007/0225487 A1 | 9/2007 | Nilsson et al. | |
| 2008/0108073 A1 | 5/2008 | Nautiyal et al. | |
| 2008/0293589 A1 | 11/2008 | Shapero | |
| 2009/0117573 A1 | 5/2009 | Fu et al. | |
| 2009/0131268 A1 | 5/2009 | Hardenbol et al. | |

(Continued)

FOREIGN PATENT DOCUMENTS

| | | |
|---|---|---|
| EP | 0964704 A1 | 12/1999 |
| WO | WO-8911548 A1 | 11/1989 |

OTHER PUBLICATIONS

NEB: "Nb.BtsI" (2013): 1. (Year: 2013).*
NEB: "Nt.BspQI" (2013): 1. (Year: 2013).*
Fuchs et al. (1989) Use of Type II Restriction Endonucleases: 25-60. (Year: 1989).*
Bellamy et al, Cleavage of Individual DNA Strands by the Different Subunits of the Heterodimeric Restriction Endonuclease BvbCI; (2005) Bellamy, S,R. Wang et al. (2005). J. Mel. Biol 345(3), pp. 641-653.
Devchand, et al. (1993) "Uracil-DNA glycosylase as a probe for protein-DNA interactions" Nucl Acids Res, 21 :3437-3443.

(Continued)

*Primary Examiner* — Jehanne S Sitton
*Assistant Examiner* — Daniel W Nielsen
(74) *Attorney, Agent, or Firm* — BioPatent Services

(57) ABSTRACT

Compositions, methods and kits are disclosed for synthesizing and amplifying pools of probes using precursor oligonucleotides. In some aspects the precursor is amplified and nicking enzymes are used to separate the full length probes from the amplification products. The methods enable the preparation of single stranded DNA probes of defined sequence and length that are suitable for use in target detection assays.

18 Claims, 12 Drawing Sheets

Specification includes a Sequence Listing.

(56) References Cited

U.S. PATENT DOCUMENTS

| | | |
|---|---|---|
| 2009/0233809 A1 | 9/2009 | Faham et al. |
| 2010/0184618 A1 | 7/2010 | Namsaraev et al. |
| 2010/0305006 A1 | 12/2010 | Kuimelis et al. |
| 2010/0311128 A1 | 12/2010 | Shapero |
| 2011/0160078 A1 | 6/2011 | Fodor et al. |
| 2011/0269631 A1 | 11/2011 | Fu et al. |
| 2011/0294689 A1 | 12/2011 | Namsaraev |
| 2012/0028826 A1 | 2/2012 | Fu et al. |
| 2013/0116130 A1 | 5/2013 | Fu et al. |

OTHER PUBLICATIONS

Fire, et al, "Rolling Replication of Short DNA Circles", Proc. Natl. Acad. Sci., (1995) vol. 92, No. 10, pp. 4641-4645.

Hardenbol et al. Highly multiplexed molecular inversion probe genotyping: over 10,000 targeted SNPs genotyped i single tube assay. Genome Res. 15, 269-275 (2005).

Hardenbol et al, "Multiplexed genotyping with sequence-tagged molecular inversion probes," Nature Biotechnology, vol. 21, No. 6, pp. 673-678 (2003).

Heiter, D. et al., "Site-Specific DNA-nicking Mutants of the Heterodimeric Restriction Endonuclease R.BbvCI", J. Mol. Biol., 348, 2005, 631-640.

Howell et al., Glucosylases and AP-cleaving enzymes as a general tool for probe-directed avage ssDNA targets: NAR (2010) 38(7):e99.

Ji, et al. (2006) "Molecular Inversion Probe Analysis of Gene Copy Alterations Reveals Distinct Categories of Colorectal Carcinoma." Cancer Res, 66(16):791 0-7919.

Levin et al, Homogeneous *Escherichia coli* Endonuclease IV, The Journal of Biological Chemistry, vol. 263, No. 17, (Jun. 15, 1988), 8066-8071.

Li, et al. (2009) "Genome-Wide Identification of Human RNA Editing Sites by Parallel DNA Capturing and Sequencing." Science, 324:1210-1213.

Lindahl, et al. (1977) "DNA N.cndot.Glycosidases, Properties of Uracil-DNA Glucosidase from *Escherichia coli*." J Biol Chem, 252(10):3286-3294.

Liu, et al. (1995) "Rolling Circle DNA Synthesis: Small Circular Oligonucleotides as Efficient Templates for DNA Polymerases." JAm Chem Soc, 118:1587-1594.

Ljungquist, S, A New Endonuclease from *Escherichia coli* acting at apurinic sites in DNA, J. Biol. Chem. 1977, 252: 2808-2814.

Li, et al. (2009) "Multiplex padlock targeted sequencing reveals human hypermutable CpG variations." Genome Res, 19(9) :1606-1615.

Marenstein et al, Human AP endonuclease (APE1) demonstrates endonucleolytic activity against AP sites in single-stranded DNA, Elsevier, DNA Repair 3 (2004), 527-533.

Margeridon et al, Rolling Circle Amplification, a Powerful Tool for Genetic and Functional Studies of Complete Hepatitis B virus Genomes from Low-Level Infections and for Directly Probing Covalently Closed Circular DNA: Antimicrobrial Agents and Chemotherapy 52(9):3068-3073 (2008).

Pease, Ann C. et al., "Light-Generated Oligonucleotide Arrays for Rapid DNA Sequence Analysis", Proc. Natl. Acad. Sci. vol. 91, May 1994, 5022-5026.

Porreca, et al., "Multiplex amplification of large sets of human exons," Nature Methods, 4(11): 931-936 (Nov. 1, 2007, Epub Oct. 14, 2007).

Samuelson, J. et al., "The isolation of strand-specific nicking endonucleases from a randomized Sapl expression library", Nucleic Acids Research, vol. 32, No. 12, 2004, pp. 3661-3671.

Tian, et al. (2004) "Accurate multiplex gene synthesis from programmable DNA microchips." Nature, 432(7020):1050-1054.

Walker et al., "Isothermal in vitro amplification of DNA by restriction enzyme/DNA polymerase system," Proceedings of the National of Academy of Sciences, vol. 89, 1992, 392-396.

Wang, et al. (2005) "Allele quantification using molecular Inversion probes (MIP)." Nucleic Acids Research 33(21):e183.

Wang, et al. (2007) "Analysis of molecular inversion probe performance for allele copy number determination." Genome Biology 8(11):R246.

Wang, et al. (2009) "High quality copy number and genotype data from FFPE samples using Molecular Inversion Probe (MIP) mIcroarrays." BMC Med Genomics, 2(8):1-13.

Wang, H. and Hays, J. (2000) "Preparation of DNA Substrates for In Vitro Mismatch Repair." Mol Biotechnol, 15(2):97-104.

Xu, et al. (2001) "Engineering a nicking endonuclease N. Alwl by domain swapping," PNAS, 98(23):12990-12995.

Zhang et al., Ramification amplification: a novel isothermal DNA amplification method; Mol. Diagn, 6:141-150 (2001), (abstract only).

Zhou, et al., "Microfluidic PicoArray synthesis of oligonucleotides and simultaneous assembling of multiple DNA sequences", Nucleic Acids Research, vol. 32, No. 18, Oct. 2004, 5409-5417.

Zhu, et al. (2004) "Engineering Strand-specific DNA Nicking Enzymes from the Type IIS Restriction Endonucleases BsaI, BsmBI, and BsmAI." J Mol Biol, 337:573-583.

\* cited by examiner

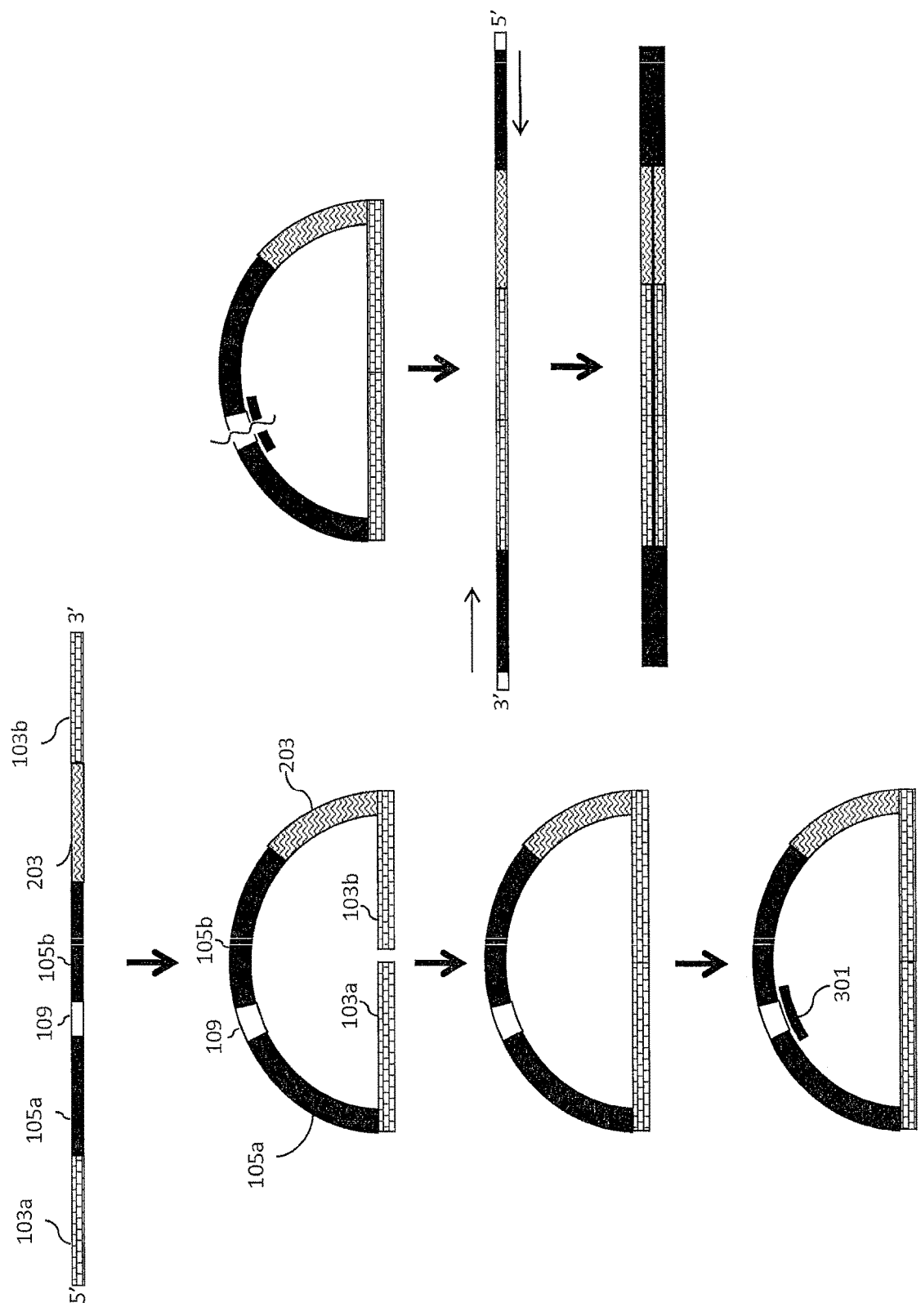

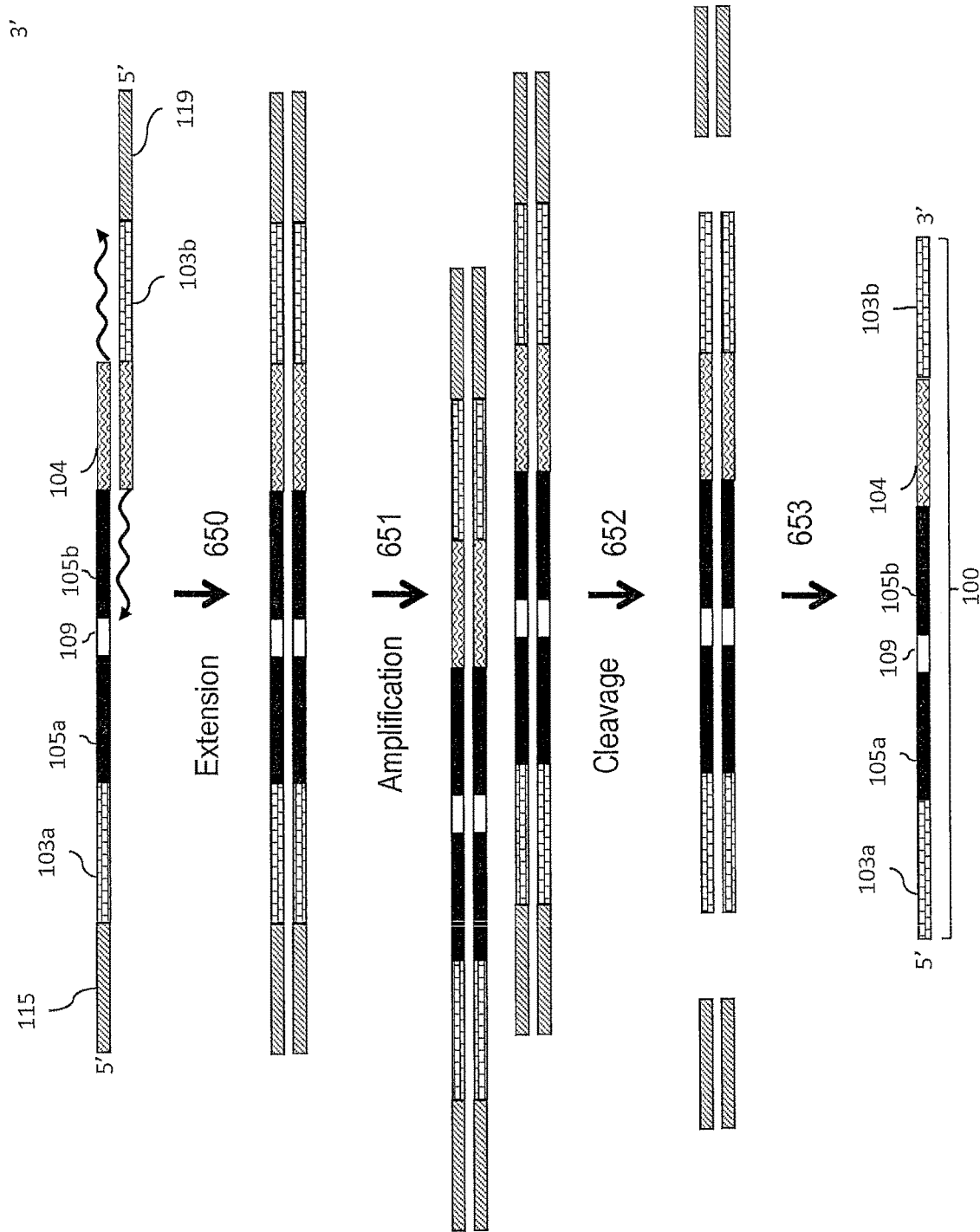

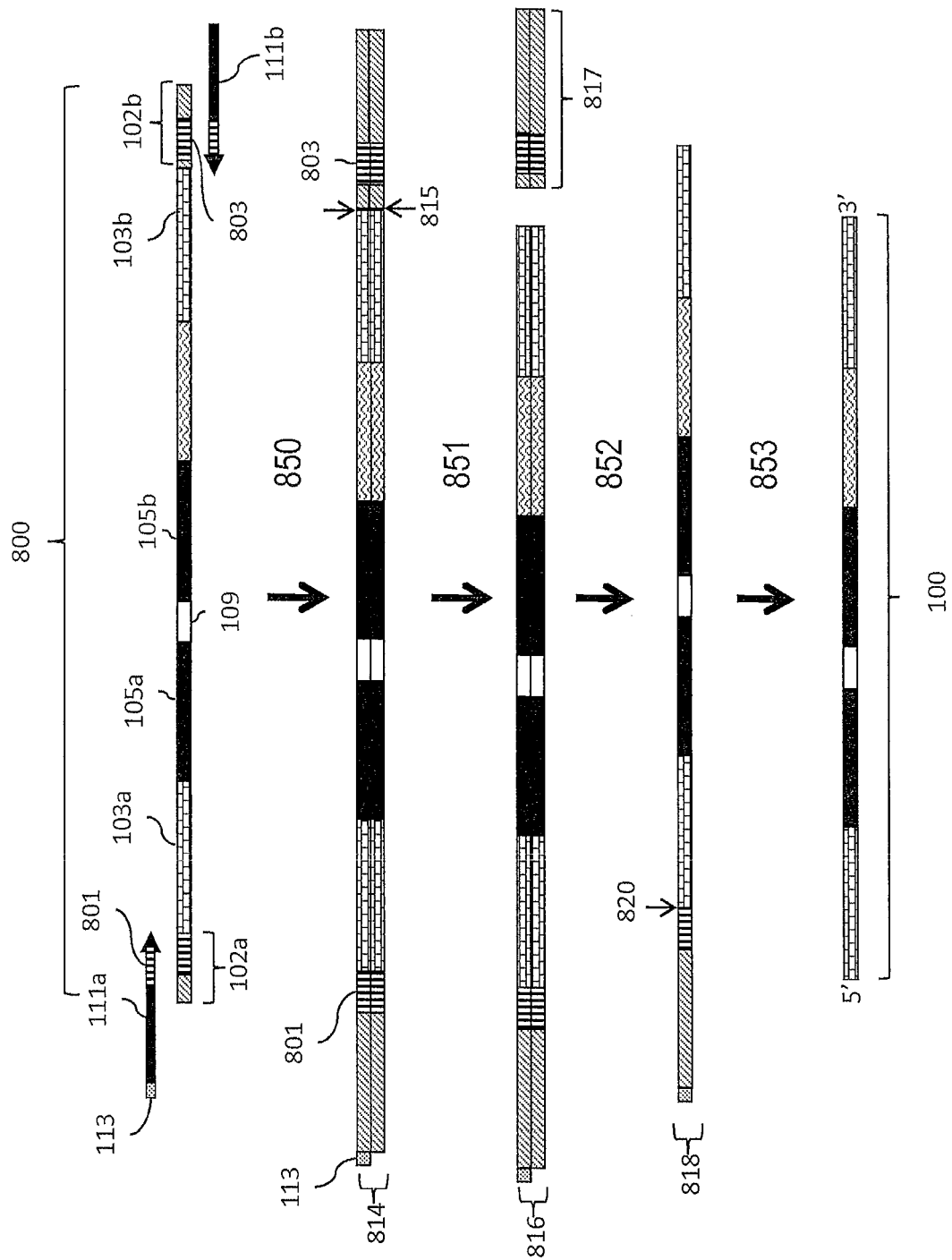

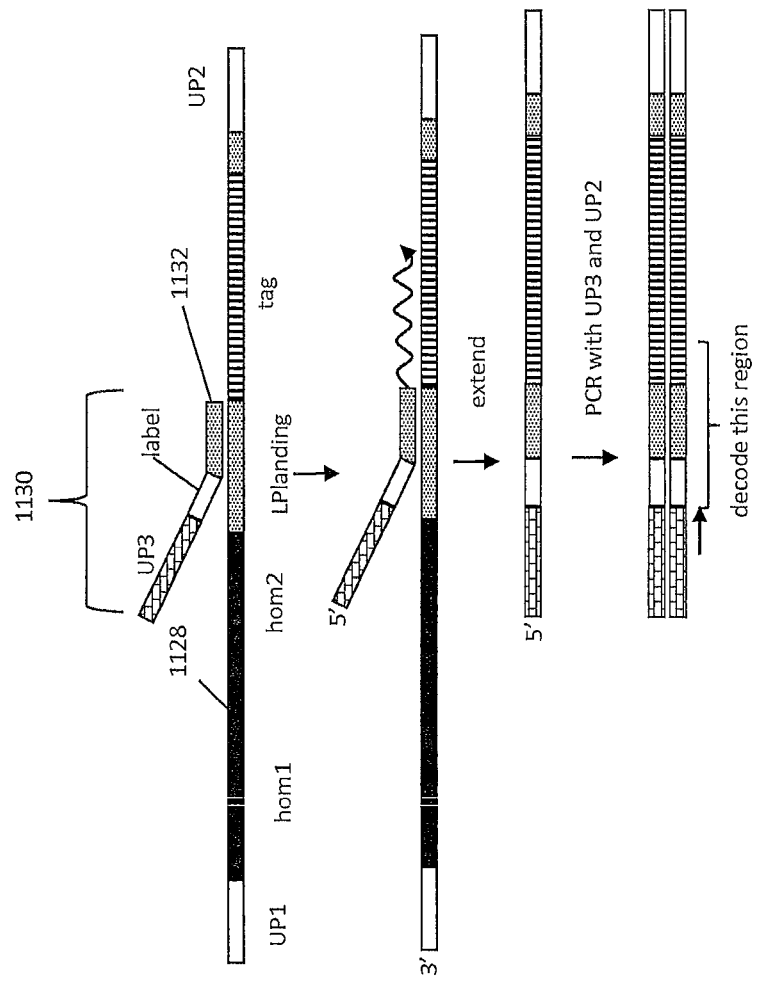

METHODS FOR SYNTHESIZING POOLS OF PROBES

RELATED APPLICATIONS

This application claims priority to U.S. Provisional application No. 61/454,914 filed Mar. 21, 2011, the entire disclosure of which is incorporated herein by reference in its entirety.

FIELD OF THE INVENTION

Methods, compositions and products for preparing pools of probes by amplification using one or more common priming regions are disclosed.

BACKGROUND OF THE INVENTION

The detection of specific nucleic acids is an important tool for diagnostic medicine and for research into disease and the function of cellular processes. It is often desirable to analyze many different targets in parallel within a single experiment. Often these multiplex methods require the use of pools of target specific probes that facilitate the specific analysis of individual targets. It is desirable that the same pool of probes may be used to analyze many different samples over time and in different locations so it is desirable to have methods for amplifying an initial pool to generate amounts of the pool sufficient to process many thousands or tens of thousands of samples.

Molecular inversion probes, also referred to as "pre-circle probes", and methods for using these probes have been disclosed, for example, in U.S. Pat. Nos. 7,700,323 and 6,858,412, the disclosures of which are incorporated herein by reference in their entireties for all purposes. The molecular inversion probe (or "MIP") preferably has the form of a single strand having a first targeting domain at the 5' end and a second targeting domain at the 3' end. Between the targeting domains the MIP preferably has a priming site to be used for subsequent amplification, and often first and second universal priming sites, and may optionally a barcode sequence or one or more cleavage sites. This is shown schematically in FIG. 1 of U.S. Pat. No. 6,858,412 and FIG. 2A of the '412 patent shows the MIP hybridized to a target in a preferred embodiment. Additional methods for synthesizing MIPs have been previously disclosed in US patent publication 20060234264 filed Mar. 14, 2006 (application Ser. No. 11/375,818) which claims priority to 60/662,032, the disclosures of which are incorporated by reference in their entireties.

SUMMARY OF THE INVENTION

A number of methods directed at generating and amplifying pools of probes useful for multiplex amplification and analysis of nucleic acid targets are disclosed herein. The methods allow for multiplex amplification of the pools of probes. Methods for separating the processed probes from precursors and by-products are also disclosed.

In one aspect probes are synthesized as oligonucleotide precursors that can be amplified in pools to generate milligram amounts of processed probe pools from nanogram amounts of precursor. This allows inexpensive and efficient synthesis methods, followed by inexpensive and efficient amplification to prepare probes, rather than more costly chemical synthesis of preparative quantities of the full length probes.

In one embodiment the precursor probe is synthesized so that the desired final probe sequence is flanked by an upstream preparative priming region and a downstream preparative priming region. When a number of probes are to be synthesized and amplified in a pool the precursor probes for all the probes in the pool preferably have the same upstream priming region and the same downstream priming region. Both preparative priming regions have recognition sites for nicking restriction enzymes arranged so that after amplification the final product can be cleaved from the double stranded amplification product. All ends of the double stranded product are labeled with an affinity selection reagent such as biotin so that the processed probe can be separated from the intermediates and byproducts.

In one aspect the precursor oligonucleotides have from the 5' end, a first preparative universal priming region with a first nicking enzyme recognition sequence, a first genomic homology region, a first analytical universal priming region, a restriction enzyme recognition sequence, a second analytical universal priming region, a second genomic homology region and a second preparative universal priming region having a second nicking enzyme recognition sequence. Within a pool the universal priming regions can be the same sequence in each of the probes with the genomic homology regions being unique to each different probe sequence or to each target.

In another aspect the precursor probes are synthesized as partially complementary precursors that each contain a portion of the desired product and each contains a 5' common preparative priming region with a restriction site. The two precursors are hybridized through a unique complementary region, for example the tag region or one of the target homology regions, and the 3' end of each is extended using the other as template. The resulting product is amplified by PCR using the preparative priming regions which are then cleaved by restriction digestion.

In another aspect, the precursors are synthesized with an additional preparative priming site at the 3' end. A primer is hybridized and extended and then the product is cleaved near the end of the primer but only in the extended strand. The primer is then extended again from the site of nicking. This is repeated, each time displacing the previously synthesized strand.

BRIEF DESCRIPTION OF THE DRAWINGS

FIG. 4 shows a schematic of the MIP assay where cleavage is at a partially double stranded cleavage site.

FIG. 6 shows a schematic of a method for synthesis of oligonucleotides by hybridization and extension of two partially complementary precursor oligonucleotides.

FIG. 8 shows a schematic of a method for synthesis of oligonucleotides using a precursor incorporating a type IIs cleavage site and a cleavage site comprising uracil.

FIG. 9B shows a schematic of labeling molecular inversion probes with stochastic labels.

DETAILED DESCRIPTION OF THE INVENTION

Figure 1A:
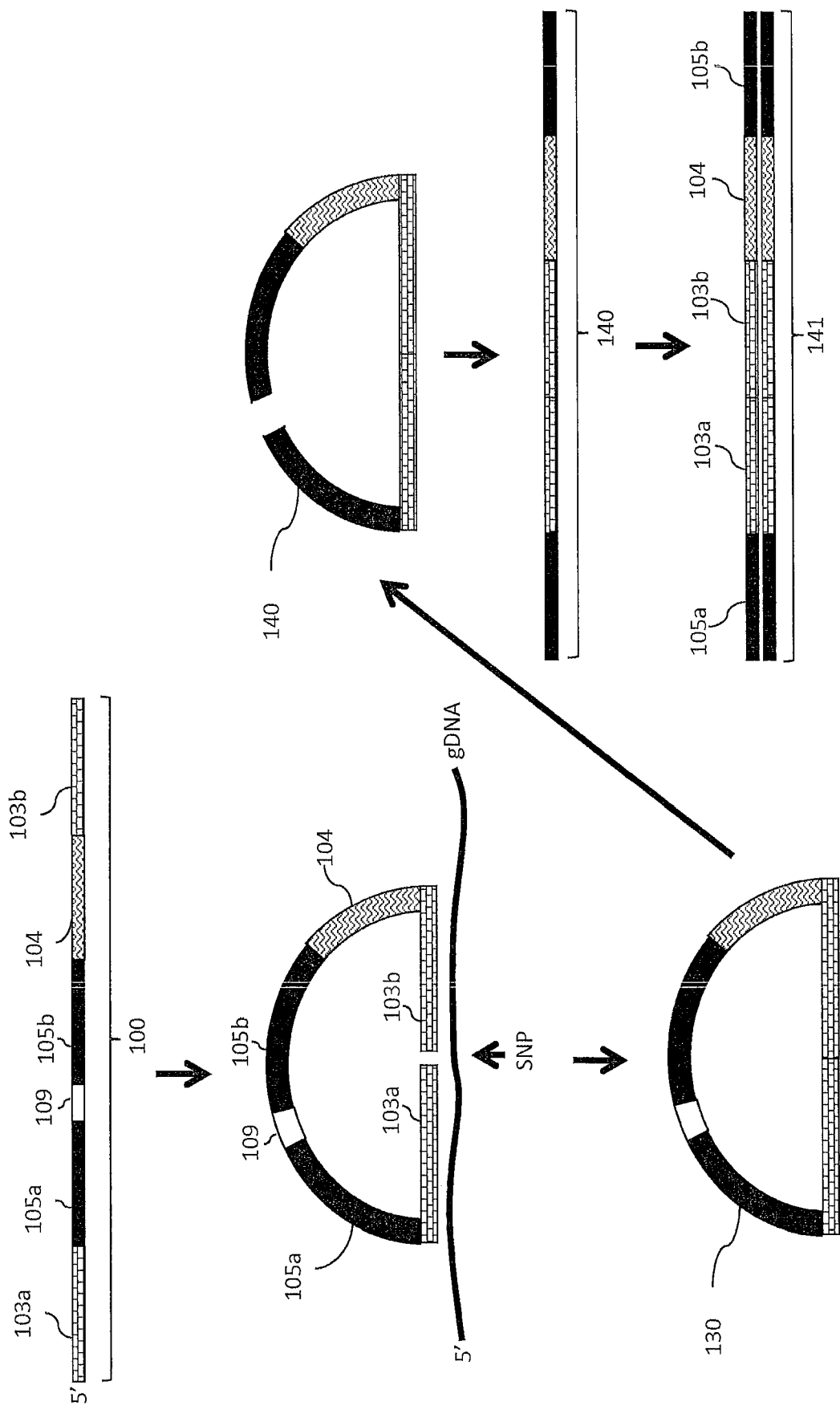
FIG. 1A shows a schematic of a MIP detection assay using a pair of universal primers separated by a cleavage site.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention has many preferred embodiments and relies on many patents, applications and other references for details known to those of the art. Therefore, when a patent, application, or other reference, such as a printed publication, is cited or repeated below, it should be understood that it is incorporated by reference in its entirety for all purposes and particularly for the proposition that is recited.

As used in this application, the singular form "a", "an", and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (*Vols. I-IV*), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Gait, *"Oligonucleotide Synthesis: A Practical Approach"* 1984, IRL Press, London, Nelson and Cox (2000), Lehninger et al., (2008) *Principles of Biochemistry* 5th Ed., W.H. Freeman Pub., New York, N.Y. and Berg et al. (2006) *Biochemistry*, $6^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Publication No. WO 99/36760 and WO 01/58593, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques may be applied to polypeptide arrays. Methods for enriching for full length oligonucleotides are disclosed, for example, in U.S. Patent Pub 20100311128 and methods for parallel probe synthesis on arrays followed by release from the array are disclosed in U.S. Patent Pub 20100305006, which are both incorporated herein by reference in their entireties.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Patent Publication Nos. 20030036069 and 20070065816 and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain embodiments. Prior to or concurrent with analysis, the sample may be amplified by a variety of mechanisms. In some aspects nucleic acid amplification methods such as PCR may be combined with the disclosed methods and systems. See, for example, *PCR Technology: Principles and Applications for DNA Amplification* (Ed. H. A. Erlich, Freeman Press, NY, NY, 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675, each of which is incorporated herein by reference in their entireties for all purposes. Enzymes and related methods of use in molecular biology that may be used in combination with the disclosed methods and systems are reviewed, for example, in Rittie and Perbal, *J. Cell Commun. Signal.* (2008) 2:25-45. The sample may be amplified on the array. See, for example, U.S. Pat. No. 6,300,070 and which is incorporated herein by reference in its entirety for all purposes.

Many of the methods and systems disclosed herein utilize enzyme activities. A variety of enzymes are well known, have been characterized and many are commercially available from one or more supplier. For a review of enzyme activities commonly used in molecular biology see, for example, Rittie and Perbal, *J. Cell Commun. Signal.* (2008) 2:25-45, incorporated herein by reference in its entirety. Exemplary enzymes include DNA dependent DNA polymerases (such as those shown in Table 1 of Rittie and Perbal), RNA dependent DNA polymerase (see Table 2 of Rittie and Perbal), RNA polymerases, ligases (see Table 3 of Rittie and Perbal), enzymes for phosphate transfer and removal (see Table 4 of Rittie and Perbal), nucleases (see Table 5 of Rittie and Perbal), and methylases.

Other methods of genome analysis and complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 and U.S. Patent Publication Nos. 20030039069, 20050079536, 20030096235, 20030082543, 20040072217, 20050142577, 20050233354, 20050227244, 20050208555, 20050074799, 20050042654, and 20040067493, which are each incorporated herein by reference in their entireties, The design and use of allele-specific probes for analyzing polymorphisms is described by e.g., Saiki et al., *Nature* 324, 163-166 (1986) and Dattagupta, EP 235,726, and WO 89/11548. Allele-specific probes can be designed that hybridize to a segment of target DNA from one individual but do not hybridize to the corresponding segment from another individual due to the presence of different polymorphic forms in the respective segments from the two individuals.

Sample preparation methods are also contemplated in many embodiments. Prior to or concurrent with analysis, the genomic sample may be amplified by a variety of mechanisms, some of which may employ PCR. See, e.g., *PCR Technology: Principles and Applications for DNA Amplification* (Ed. H.A. Erlich, Freeman Press, NY, NY, 1992); PCR Protocols: *A Guide to Methods and Applications* (Eds. Innis, et al., *Academic Press*, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188,and 5,333,675, and each of which is incorporated herein by reference in their entireties for all purposes. See also U.S. Pat. No. 6,300,070 which is incorporated herein by reference. Additional methods of sample preparation and techniques for reducing the complexity of a nucleic sample are described in Dong et al., *Genome Research* 11, 1418 (2001), in U.S. Pat. No. 6,361,947, 6,391,592 and U.S. Patent Pub. Nos. 20030096235, 20030082543 and 20030036069.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, PNAS 92:4641 (1995) and Liu et al., J. Am. Chem. Soc. 118:1587 (1996)) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 6,582,938, 5,242,794, 5,494,810, 4,988,617, and US Pub. No. 20030143599 each of which is incorporated herein by reference.

Molecular inversion probes may also be used for amplification of selected targets. MIPs may be generated so that the ends of the pre-circle probe are complementary to regions that flank the region to be amplified. The region can be, for example, between 1 and 2,000 bases or more. The gap can be closed by extension of the end of the probe so that the complement of the target is incorporated into the MIP prior to ligation of the ends to form a closed circle. The closed circle can be amplified as previously disclosed in Hardenbol et al. *Nat Biotechnol.* 21:673-8 (2003), Hardenbol et al., *Genome Res.* 15:269-275 (2005), Ji et al. *Cancer Res* 66:7910-9, and in U.S. Pat. No. 6,858,412, all of which are incorporated herein by reference in their entireties.

In some embodiments, amplification may include the use of a strand displacing polymerase that may be primed by selected primers or by a mixture of primers, for example, random hexamers. See for example Lasken and Egholm, *Trends Biotechnol.* 2003 21(12):531-5; Barker et al. *Genome Res.* 2004 May;14(5):901-7; Dean et al. *Proc Natl Acad Sci USA.* 2002; 99(8):5261-6; and Paez, J. G., et al. *Nucleic Acids Res.* 2004; 32(9):e71. Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. DNA may also be amplified by multiplex locus-specific PCR or using adaptor-ligation and single primer PCR. Other available methods of amplification, such as balanced PCR (Makrigiorgos, et al. (2002), *Nat Biotechnol*, Vol. 20, pp.936-9), may also be used.

Methods of ligation will be known to those of skill in the art and are described, for example in Sambrook et at. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'->5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation. For a review of ligation based methods see also Conze et al. *Annu Rev Anal Chem* (2009) 2:215-239.

Fixed content mapping arrays are available from Affymetrix, for example, the SNP 6.0 array. Methods for using mapping arrays see, for example, Kennedy et al., *Nat. Biotech.* 21:1233-1237 (2003), Matsuzaki et al., *Genome Res.* 14:414-425 (2004), Matsuzaki et al., *Nat. Meth.* 1:109-111 (2004) and U.S. Patent Pub. Nos. 20040146890 and 20050042654, each incorporated herein by reference. Applications of microarrays for SNP genotyping have been described in e.g., U.S. Pat. Nos. 6,300,063, 6,361,947, 6,368,799 and US Patent Publication Nos. 20040067493, 20030232353, 20030186279, 20050260628, 20070065816 and 20030186280, all incorporated herein by reference in their entireties for all purposes.

Selected panels of SNPs can also be interrogated using a panel of locus specific probes in combination with a universal array as described in Hardenbol et al., *Genome Res.* 15:269-275 (2005) and in U.S. Pat. No. 6,858,412. Universal tag arrays and reagent kits for performing such locus specific genotyping using panels of custom molecular inversion probes (MIPs) are available from Affymetrix.

Computer implemented methods for determining genotype using data from mapping arrays are disclosed, for example, in Liu, et al., *Bioinformatics* 19:2397-2403 (2003), Rabbee and Speed, *Bioinformatics,* 22:7-12 (2006), and Di et al., *Bioinformatics* 21:1958-63 (2005). Computer implemented methods for linkage analysis using mapping array data are disclosed, for example, in Ruschendorf and Nurnberg, *Bioinformatics* 21:2123-5 (2005) and Leykin et al., *BMC Genet.* 6:7, (2005). Computer methods for analysis of genotyping data are also disclosed in U.S. Patent Pub. Nos. 20060229823, 20050009069, 20040138821, 20060024715, 20050250151 and 20030009292.

Methods for analyzing chromosomal copy number using mapping arrays are disclosed, for example, in Bignell et al., *Genome Res.* 14:287-95 (2004), Lieberfarb, et al., *Cancer Res.* 63:4781-4785 (2003), Zhao et al., *Cancer Res.* 64:3060-71 (2004), Huang et al., *Hum Genomics* 1:287-299 (2004), Nannya et al., *Cancer Res.* 65:6071-6079 (2005), Slater et al., *Am. J. Hum. Genet.* 77:709-726 (2005) and Ishikawa et al., *Biochem. and Biophys. Res. Comm.,* 333: 1309-1314 (2005). Computer implemented methods for estimation of copy number based on hybridization intensity are disclosed in U.S. Patent Pub. Nos. 20040157243, 20050064476, 20050130217, 20060035258, 20060134674 and 20060194243.

Methods for using molecular inversion probes for copy number analysis from FFPE samples have been disclosed, for example, in Wang Y., et al. *BMC Medical Genomics* 2:8 (2009). Methods for using the MIP assay for allele specific copy number determination have been shown, for example, in Wang Y., et al. *Genome Biology* 8(11):R246 (2007) and Wang Y., et al. *Nucleic Acids Research* 33(21):e183 (2005). Methods for using the MIP assay for analysis of gene copy number variation have been disclosed for example in Ji H., et al. *Cancer Research* 66(16):7910-9 (2006).

Additional methods of sample preparation and techniques for reducing the complexity of a nucleic sample are described in Dong et al., *Genome Research* 11, 1418 (2001), in U.S. Pat. Nos. 6,361,947, 6,391,592 and 6,872,529 and U.S. Patent Publication Nos. 20030036069, 20030096235 and 20030082543. Additional methods of using a genotyping array are disclosed, for example, in U.S. Patent Publication Nos. 20040146883, 20030186280, 20030186279, 20040067493, 20030232353, 20060292597, 20050233354, 20050074799, 20070065816 and 20040185475.

Methods for conducting polynucleotide hybridization assays have been well developed in the art. Hybridization assay procedures and conditions will vary depending on the application and are selected in accordance with known general binding methods, including those referred to in: Maniatis et al. *Molecular Cloning: A Laboratory Manual* (2$^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davis, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Patent Pub. No. 20040012676 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Patent Pub. Nos. 20040012676 and 20050059062 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Additionally, the present disclosure may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus. Genotypes are often referred to using the following nomenclature, "AA" for homozygous for the A allele, "BB" for homozygous for the B allele and "AB" for heterozygous. The major allele is the allele that is most prevalent in a population and the minor allele is the allele that is less prevalent. For example if a SNP has two forms, C or G, in a population and the C allele is present a 70% frequency in the population and the G allele is present at 30%, the C allele is the major allele and the G allele is the minor allele.

Single nucleotide polymorphisms (SNPs) are positions at which two alternative bases occur at appreciable frequency (>1%) in a given population. SNPs are a common type of human genetic variation and are useful in the performance of genome wide association studies (GWAS). GWAS may be used, for example for the analysis of biological pathways, see Wang and Hakonarson, *Nat. Rev. Genet.* 2010, 11:843-854. Other common variation includes single base deletions or insertions of a nucleotide relative to a reference allele. Copy number variants (CNVs), transversions and other rearrangements are also forms of genetic variation.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs or CNVs. A diploid individual may be homozygous for each of the two possible alleles (for example, AA or BB) or heterozygous (for example, AB). For additional information regarding genotyping and genome structure see, *Color Atlas of Genetics*, Ed. Passarge, Thieme, New York, N.Y. (2001), which is incorporated by reference.

Normal cells that are heterozygous at one or more loci may give rise to tumor cells that are homozygous at those loci. This loss of heterozygosity (LOH) may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, microparticles, nanoparticles or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. See, M. Kanehisa Nucleic Acids Res. 12:203 (1984), incorporated herein by reference.

The term "copy number variation" or "CNV" refers to differences in the copy number of genetic information. In many aspects it refers to differences in the per genome copy number of a genomic region. For example, in a diploid organism the expected copy number for autosomal genomic regions is 2 copies per genome. Such genomic regions should be present at 2 copies per cell. For a recent review see Zhang et al. *Annu. Rev. Genomics Hum. Genet.* 2009. 10:451-81. CNV is a source of genetic diversity in humans and can be associated with complex disorders and disease, for example, by altering gene dosage, gene disruption, or gene fusion. They can also represent benign polymorphic variants. CNVs can be large, for example, larger than 1 Mb, but many are smaller, for example between 100 bp and 1 Mb. More than 38,000 CNVs greater than 100 bp (and less than 3 Mb) have been reported in humans. Along with SNPs these CNVs account for a significant amount of phenotypic variation between individuals. In addition to having deleterious impacts, e.g. causing disease, they may also result in advantageous variation.

Digital PCR is a technique where a limiting dilution of the sample is made across a large number of separate PCR reactions so that most of the reactions have no template molecules and give a negative amplification result. Those reactions that are positive at the reaction endpoint are counted as individual template molecules present in the original sample in a 1 to 1 relationship. See Kalina et al. *NAR* 25:1999-2004 (1997) and Vogelstein and Kinzler, *PNAS* 96:9236-9241 (1999). This method is an absolute counting method where solutions are partitioned into containers until there is an average probability of one molecule per two containers or when, $P_0=(1-e^{-n/c})=\frac{1}{2}$; where n is the number of molecules and c is the number of containers, or n/c is 0.693. Quantitative partitioning is assumed, and the dynamic range is governed by the number of containers available for stochastic separation. The molecules are then detected by PCR and the number of positive containers is counted. Each successful amplification is counted as one molecule, independent of the actual amount of product. PCR-based techniques have the additional advantage of only counting molecules that can be amplified, e.g. that are relevant to the massively parallel PCR step in the sequencing workflow. Because digital PCR has single molecule sensitivity, only a few hundred library molecules are required for accurate quantification. Elimination of the quantification bottleneck reduces the sample input requirement from micrograms to nanograms or less, opening the way for minute and/or precious samples onto the next-generation sequencing platforms without the distorting effects of pre-amplification. Digital PCR has been used to quantify sequencing libraries to eliminate uncertainty associated with the construction and application of standard curves to PCR-based quantification and enable direct sequencing without titration runs. See White et al. *BMC Genomics* 10: 116 (2009). To vary dynamic range, micro-fabrication can be used to substantially increase the number of containers. See, Fan et al. *Am J Obstet Gynecol* 200, 543 el (May, 2009).

Similarly, in stochastic labeling, the same statistical conditions are met when $P_0=(1-e^{-n/m})=\frac{1}{2}$; where in is the number of labels, and one half of the labels will be used at least once when n/m=0.693. The dynamic range is governed by the number of labels used, and the number of labels can be easily increased to extend the dynamic range. The number of containers in digital PCR plays the same role as the number of labels in stochastic labeling and by substituting containers for labels identical statistical equations may be applied. Using the principles of physical separation, digital PCR stochastically expands identical molecules into physical space, whereas the principle governing stochastic labeling is identity based and expands identical molecules into identity space.

"FFPE" or formalin fixed paraffin embedded refers to a process used for preservation of tissue samples over the last approximately 75 years. Sample DNA from such samples can be damaged by the exposure to formaldehyde and a potentially acidic environment. Often the DNA fragments in such samples are degraded into short fragments that are less suitable for analysis by some amplification methods. The samples can also contain chemical damage and modifications that may inhibit enzyme dependent chemistries. See, Gilbert et al. PLoS One 2(6):e537 (2007). The FFPE samples also may contain limiting amounts of DNA. Compared to fresh frozen samples, FFPE derived samples, raise significant challenges for reliable analysis. Methods, such as the MIP assay, that are capable of analyzing FFPE samples are highly useful.

The term "hybridization" as used herein refers to the process in which two single-stranded polynucleotides bind noncovalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations may be performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above. In some aspects salt concentrations for hybridization are preferably between about 200 mM and about 1M or between about 200 mM and about 500 mM. Hybridization temperatures can be as low as 5° C. , but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nicking enzyme" as used herein refers to an enzyme that can be used to cleave one strand of a double stranded duplex. Restriction endonucleases generally recognize specific sequences in double-stranded DNA and cleave both strands. Some however cleave only one of the strands. These nicking endonucleases have been discovered as naturally occurring enzymes and have been genetically engineered. Examples of an engineered enzyme include Nt.BbvCI and Nb.BbvCI. These are mutants of the heterodimeric BbvCI enzyme. The "Nb" version cleaves only the bottom strand and the "Nt" version cleaves only the top strand. More than 200 nicking enzymes have been described and more than 13 are available commercially. The following are available from NEB: Nt.CviPII, Nb. BsmI, Nb.BbvCI, Nb.BsrDI, Nb.BtsI, Nt.BsmAI, Nt.BbvCI, Nt.BspQI, Nt.AlwI, and Nt.BstNBI. For additional discussion regarding nicking enzymes see Bellamy et al. (2005) Bellamy, S. R. W. et al. (2005) *J. Mol. Biol.* 345, 641-653, Heiter, D. F., Lunnen, K. D. and Wilson, G. G. (2005) *J. Mol. Biol.* 348, 631-640, Xu, Y. et al. (2001) *Proc. Natl. Acad. Sci.* USA 98, 12990-12995, Samuelson, J. C., Zhu, Z. and Xu, S. Y. (2004) *Nucl. Acids Res.* 32, 3661-3671 and Zhu, Z. et al. (2004) *J. Mol. Biol.* 337, 573-583, which are each incorporated herein by reference in their entireties.

The nicks generated by cleavage with a nicking enzyme (3'-hydroxyl, 5'-phosphate) can serve as initiation points for further enzymatic reactions such as replacement DNA synthesis, strand-displacement amplification (Walker, G. T. et al. (1992) *Proc. Natl. Acad. Sci. USA* 89, 392-396.), exonucleolytic degradation or the creation of small gaps (Wang, H. and Hays, J. B. (2000) *Mol. Biotechnol.* 15, 97-104). These enzymes may occur naturally or they may be engineered or altered to nick. N.BstNB I occurs naturally and nicks because it is unable to form dimers. N.Alw I is a derivative of the restriction enzyme Alw I, that has been engineered to behave in the same way. These enzymes nick adjacent to their recognition sequences. N.BbvC IA and N.BbvC IB are derived from the heterodimeric restriction enzyme BbvC I, each has only one catalytic site so they nick within the recognition sequence but on opposite strands. It is likely that the methods used to engineer existing nicking enzymes will be broadly applicable and many existing restriction enzymes may be engineered to produce corresponding nicking enzymes. Nicking sites may also be engineered by including hemiphosphorothioate sites as described in Walker, G. T. et al. (1992) Proc. Natl. Acad. Sci. USA 89, 392-396.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "Strand Displacement Amplification" (SDA) is an isothermal in vitro method for amplification of nucleic acid. In general, SDA methods initiate synthesis of a copy of a nucleic acid at a free 3' OH that may be provided, for example, by a primer that is hybridized to the template. The DNA polymerase extends from the free 3' OH and in so doing, displaces the strand that is hybridized to the template leaving a newly synthesized strand in its place. Subsequent rounds of amplification can be primed by a new primer that hybridizes 5' of the original primer or by introduction of a nick in the original primer. Repeated nicking and extension with continuous displacement of new DNA strands results in exponential amplification of the original template. Methods of SDA have been previously disclosed, including use of nicking by a restriction enzyme where the template strand is resistant to cleavage as a result of hemimethylation. Another method of performing SDA involves the use of "nicking" restriction enzymes.

Polymerases useful for SDA generally will initiate 5' to 3' polymerization at a nick site, will have strand displacing activity, and preferably will lack substantial 5' to 3' exonuclease activity. Enzymes that may be used include, for example, the Klenow fragment of DNA polymerase I, Bst polymerase large fragment, Phi29, and others. DNA Polymerase I Large (Klenow) Fragment consists of a single polypeptide chain (68 kDa) that lacks the 5' to 3' exonuclease activity of intact E. coli DNA polymerase I. However, DNA Polymerase I Large (Klenow) Fragment retains its 5' to 3' polymerase, 3' to 5' exonuclease and strand displacement activities. The Klenow fragment has been used for SDA. For methods of using Klenow for SDA see, for example, U.S. Pat. Nos. 6,379,888; 6,054,279; 5,919,630; 5,856,145; 5,846,726; 5,800,989; 5,766,852; 5,744,311; 5,736,365; 5,712,124; 5,702,926; 5,648,211; 5,641,633; 5,624,825; 5,593,867; 5,561,044; 5,550,025; 5,547,861; 5,536,649; 5,470,723; 5,455,166; 5,422,252; 5,270,184, the disclosures of which are incorporated herein by reference. Examples of other enzymes that may be used include: exo minus Vent (NEB), exo minus Deep Vent (NEB), Bst (BioRad), exo minus Pfu (Stratagene), Pfx (Invitrogen), 9° N™. (NEB), and other thermostable polymerases.

Phi29 is a DNA polymerase from *Bacillus subtilis* that is capable of extending a primer over a very long range, for example, more than 10 Kb and up to about 70 Kb. This enzyme catalyzes a highly processive DNA synthesis coupled to strand displacement and possesses an inherent 3' to 5' exonuclease activity, acting on both double and single stranded DNA. Variants of phi29 enzymes may be used, for example, an exonuclease minus variant may be used. Phi29 DNA Polymerase optimal temperature range is between about 30° C. to 37° C., but the enzyme will also function at higher temperatures and may be inactivated by incubation at about 65° C. for about 10 minutes. Phi29 DNA polymerase and Tina Endonuclease V (available from Fermentas Life Sciences) are active under compatible buffer conditions. Phi29 is 90% active in NEBuffer 4 (20 mM Tris-acetate, 50 mM potassium acetate, 10 mM magnesium acetate and 1 mM DTT, pH 7.9 at 25° C.) and is also active in NEBuffer 1 (10 mM Bis-Tris-Propane-HCl, 10 mM magnesium chloride and 1 mM DTT, pH 7.0 at 25° C.), NEBuffer 2 (50 mM sodium chloride, 10 mM Tris-HCl, 10 mM magnesium chloride and 1 mM DTT, pH 7.9 at 25° C.), NEBuffer 3 (100 mM NaCl, 50 mM Tris HCl, 10 mM magnesium chloride and 1 mM DTT, pH 7.9 at 25° C.). For additional information on phi29, see U.S. Pat. Nos. 5,100,050, 5,198,543 and 5,576,204.

Bst DNA polymerase originates from Bacillus stearothennophilus and has a 5' to 3' polymerase activity, but lacks a 5' to 3' exonuclease activity. This polymerase is known to have strand displacing activity. The enzyme is available from, for example, New England Biolabs. Bst is active at high temperatures and the reaction may be incubated optimally at about 65° C. but also retains 30%45% of its activity at 50° C. Its active range is between 37° C.-80° C. The enzyme tolerates reaction conditions of 70° C. and below and can be heat inactivated by incubation at 80° C. for 10 minutes. Bst DNA polymerase is active in the NEBuffer 4 (20 mM Tris-acetate, 50 mM potassium acetate, 10 mM magnesium acetate and 1 mM DTT, pH 7.9 at 25° C.) as well as NEBuffer 1(10 mM Bis-Tris-Propane-HCl, 10 mM magnesium chloride and 1 mM DTT, pH 7.0 at 25° C.), NEBuffer 2(50 mM sodium chloride, 10 mM Tris-HCl, 10 mM magnesium chloride and 1 mM DTT, pH 7.9 at 25° C.), and NEBuffer 3(100 mM NaCl, 50 mM Tris HCl, 10 mM magnesium chloride and 1 mM DTT, pH 7.9 at 25° C.). Bst DNA polymerase could be used in conjunction with *E. coli* Endonuclease V (available from New England Biolabs). For additional information see Mead, D. A. et al. (1991) BioTechniques, p.p. 76-87, McClary, J. et al. (1991) J. DNA Sequencing and Mapping, p.p. 173-180 and Hugh, G. and Griffin, M. (1994) PCR Technology, p.p. 228-229.

The term "UDG" or "UNG" refers to the enzyme uracil DNA glycosylase. UDG catalyses the release of free uracil from uracil-containing DNA. UDG hydrolyzes uracil from single-stranded or double-stranded DNA. See Lindahl, et al. (1977) J. Biol. Chem., 252, 3286-3294 and Devchand et al., (1993) Nucl. Acids Res., 21, 3437-3443, which are incorporated herein by reference in their entireties. The function of the enzyme in nature is to eliminate uracil bases from DNA by cleaving the N-glycosylic bond and initiating the base-excision repair pathway. UDG specifically recognizes uracil and removes it by hydrolyzing the N-Cl' glycosylic bond linking the uracil base to the deoxyribose sugar. The loss of the uracil creates an abasic site (also known as an AP site or apurinic/apyrimidinic site) in the DNA. An abasic site is a major form of DNA damage resulting from the hydrolysis of the N-glycosylic bond between a 2-deoxyribose residue and a nitrogenous base. This site can be generated spontaneously or as described above, via UDG catalyzed hydrolysis See Marenstein et al. (2004) DNA Repair 3:527-533. Treatment of the sample DNA molecule or sample nucleic acid with alkaline solutions or enzymes, such as but not limited to apurinic/apyrimidinic endonucleases, for example APE1, will cause controlled breaks in the DNA at the abasic site. See U.S. Pat. No. 6,713,294. High temperature or high pH induced hydrolysis can generate cleavage at abasic sites, although the resulting 3' termini of the cleavage may not be a substrate for labeling by TdT. An apurinic/apyrimidinic endonuclease can cleave the DNA molecule or nucleic acid at the site of the dU residue yielding fragments possessing a 3'-OH termini, thus allowing for subsequent terminal labeling. One such apurinic/apyrimidinic endonuclease is *E. coli* Endo IV which catalyzes the formation of single-strand breaks at apurinic and apyrimidinic sites within a double-stranded DNA to yield 3'-OH termini suitable for terminal labeling. *E. coli* Endo IV may also be used to remove 3' blocking groups (e.g. 3'-phosphoglycolate and 3'-phosphate) from damaged ends of double-stranded DNA. See Levin, J. D., J. Biol. Chem., 263:8066-8071 (1988) and Ljungquist, et al., J. Biol. Chem., 252:2808-2814 (1977). See also, US Patent Pub. 20070218478 and Howell et al. NAR (2010) 38(7):e99 which is incorporated herein by reference in its entirety for all purposes.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 and US Patent Pub. Nos. 20090149340 and 20080038559 for exemplary substrates.

In some aspects separation of products based on affinity selection employs a solid support. By "purification moiety" herein is meant a moiety which can be used to purify a strand of nucleic acid, usually via attachment to a solid support as outlined herein. Suitable purification moieties include members of binding partner pairs. For example, one binding partner may be a hapten or antigen, which will bind its binding partner. In a preferred embodiment, the binding partner can be attached to a solid support. For example, suitable binding partner pairs include, but are not limited to: antigens, for example proteins or peptides, and antibodies, proteins and small molecules, including biotin/streptavidin or avidin; protein-protein interacting pairs; receptor-ligand pairs; and carbohydrates and their binding partners. Nucleic acid-nucleic acid binding proteins pairs are also useful. In general, the smaller of the pair is attached to the NTP for incorporation into the primer or nucleic acids. Preferred binding partner pairs include, but are not limited to, biotin or imino-biotin and streptavidin, digoxigenin, fluorescein, dinitrophenol and derivatives thereof. The second member of the pair may be an antibody to the first binding partner. For some applications imino-biotin may be preferred as imino-biotin disassociates from streptavidin in pH 4.0 buffer while biotin requires harsh denaturants (e.g. 6 M guanidinium HCl, pH 1.5 or 90% formamide at 95° C.).

Terminal-transferase end-labeling techniques can be used to add labeled nucleotides to the ends of nucleic acids. A nucleotide labeled with a secondary label (e.g. a binding ligand, such as biotin) is added to a terminus of the target nucleic acid; supports coated or containing the binding partner (e.g. streptavidin) can thus be used to immobilize the target nucleic acid. Alternatively, the terminal transferase can be used to add nucleotides with special chemical functionalities that can be specifically coupled to a support. Preferred embodiments utilize the addition of biotinylated nucleotides followed by capture on streptavidin coated magnetic beads. In some embodiments the probe or primer are synthesized with biotinylated nucleotides or biotinylated after synthesis.

METHODS FOR SYNTHESIS OF POOLS OF PROBES

The molecular inversion probe assay has been used for a variety of applications including genotyping and copy number analysis. The method can be applied to samples that are degraded or partially degraded and is particularly useful for analysis of FFPE samples. See, Wang et al. *BMC Medical Genomics* 2:8 (2009), which is incorporated herein by reference in its entirety and demonstrates the use of MIP for copy number analysis of FFPE samples. In particular the small footprint of MIPs of about 40 base pair, the ability to use the assay with relatively small amounts of starting DNA, about 75 ng, and the ability to simultaneously analyze multiple types of variations, including copy number, genotype and somatic mutations, in a single assay make this assay particularly well suited for analysis of FFPE samples and in particular tumor samples. Methods are disclosed herein that may be applied to synthesizing large number of single stranded probes from precursor probes that may be chemically synthesized. The methods will be described here with reference to production of molecular inversion probes, but the methods can be applied to production of other nucleic acid probes as well.

MIPs are characterized by their ability to form a closed circle after hybridization to a selected target sequence, with or without a gap fill reaction, as described in U.S. Pat. No. 6,858,412, which is incorporated herein by reference in its entirety. An example of a MIP and a MIP detection assay is shown in FIG. 1A. The MIP 100 shown has a 5' target homology region 103a (also referred to as "H1"), and a 3' target homology region 103b (also referred to as "H2"). The homology regions are complementary to non-overlapping regions in the target, H1' and H2'. H1' is 5' of H2' in the target so that when the MIP is hybridized to a target, for example a genomic DNA (gDNA) target, as shown in FIG. 1A, the MIP forms a pre-circle structure as shown. The region between H1 and H2 in the MIP preferably includes at least a first priming site 105a and may include a second priming site 105b, optionally a tag sequence 104 is included, typically between one of the target specific regions and one of the universal priming regions as shown. Preferably MIPs have at least one cleavage site 109 between the priming sequences 105a and 105b. There may also be a second priming site between the tag 104 and the second homology region 103b, although not shown in the figure. The priming sequences 105a and 105b are preferably universal and common to all or many MIPs in a collection, pool or panel of MIPs. The tag sequence 104 is preferably unique for each MIP but can be characteristic of a category of targets. The MIP can be allele specific with each MIP having a different tag. MIPs can also include multiple tags, for example, a tag that is unique for each MIP and another that is characteristic of a category of MIP targets where the pool or panel may include a plurality of categories each identified by a different tag that is common to all MIPs in the category. The second tag may also be indicative of the sample or individual from which the sample is derived.

The MIP is hybridized, preferably in a multiplex fashion to target nucleic acids, e.g. many MIPs hybridized to a complex sample so that individual MIPs find their cognate targets and hybridize to those targets. Hybridization juxtaposes the ends of the MIP as shown in FIG. 1A leaving a gap between the ends of the hybridized MIP that can be closed by ligation with or without extension of the 3' end of the MIP depending on the size of the gap. In one aspect the gap is a single base corresponding to a SNP as shown and the gap is filled by a nucleotide that is complementary to the base at the SNP and then the ends of the MIP are ligated to form a closed circle 130. The closed circle can be cleaved at cleavage site 109 to form an inverted open circle 140 that can be amplified using primers to the priming regions 105a and 105b to form PCR product 141.

The PCR product or some portion thereof can be detected. In one aspect, the detection is by hybridization to an array of probes that are complementary to the tags 104. The PCR product 141 can be detected directly or it can be cleaved and a portion detected. For example, the product can be cleaved between the tag 104 and the H2 region 103b to separate the region containing the tag 104 and the second priming site 105b. That region can be hybridized to an array so that one strand hybridizes.

The MIP technology allows for large numbers of targets to be analyzed in a multiplex format by using pools of many different MIP sequences, each specific for a different target. The pools may have 100-1,000, 1,000-10,000, 10,000-100,000, 100,000-500,000 or more than 500,000 different MIP sequences. Two or more pools can be combined to form a pooled-pool. Within a pool the final or product probes (after processing from the precursor probes) may have common regions and variable regions. For example, all product probes in a pool may have the same common or universal analytical primer sites, e.g. 105a and 105b. The cleavage region 109 may be common to all probes in a pool as well. The target homology regions 103a and 103b are variable between probes and are designed to be complementary to different targets. For each target there may be a different product probe having common priming and cleavage regions that are common to all probes in the pool and variable target homology and tag/barcode regions that are different for each probe in the pool. The preparative regions in the precursor probes may be common to all precursor probes in a pool.

Figure 1B:
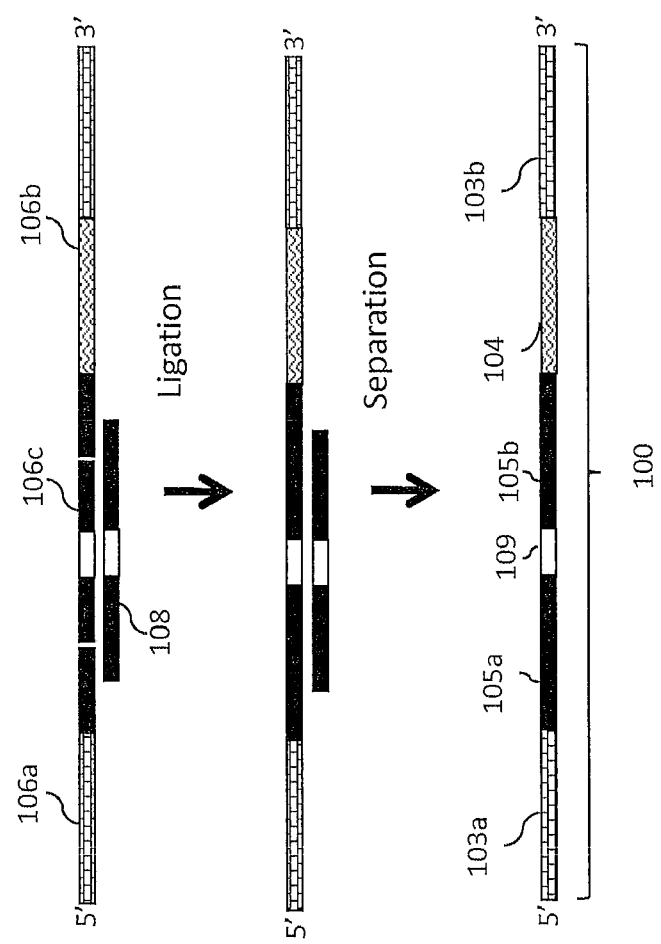
FIG. 1B shows a ligation based method for synthesizing MIPs using a splint sequence.

One method to synthesize pools of MIPs is by synthesizing the probe in 3 separate pieces and ligating the pieces together using a splint oligonucleotide. This method is illustrated in FIG. 1B. For each unique MIP there are two MIP-specific probes synthesized, A (106a) and B (106b) and two common probes, F (106c) and C (108). The C oligo is used as a splint to which A, B and F hybridize so that A and F and F and B can be ligated together to form A-F-B (the full length MIP 100). The 3' end of A ligates to the 5' end of F and the 3' end of F ligates to the 5' end of B. F is fully complementary to C, and A and B have regions that are complementary to C. The F oligo in some embodiments includes uracil bases that can be used during the MIP assay as the cleavage site 109. A and B are different for each MIP and F and C are constant. A contains the upstream homology region 103a. B contains the tag 104 and the downstream homology region 103b. C forms a splint that brings together the ends of A and B with F and does not form part of the final MIP. F is fully complementary to C and includes first and second constant primer sequences 105a and 105b for use in the PCR amplification of the MIP product after circularization. Between the first and second priming regions the F oligo typically includes a cleavage site 109. Preferably this is a site that includes one or more uracil bases but can also be a restriction site. Preferably the cleavage site can be cleaved when single stranded, but may be a site that must be double stranded for cleavage. An oligonucleotide can be hybridized to the site to make it double stranded for cleavage. The 3' end of A is complementary to the 3' end of C and the 5' end of B is complementary to the 5' end of C.

Oligos A, B and F hybridize to oligo C to form the structure in the upper portion of FIG. 1B. The hybridized complex is subjected to ligation so that A is joined to F and F to B, thus generating the full length MIP as the upper strand. The strands may be separated, for example, by size selection or by affinity selection. One of the oligos, A, B or F, may contain an affinity selectable reagent such as biotin to facilitate binding of the MIP to a matrix for separation from oligo C, or oligo C may have the affinity selectable reagent facilitating separation of C from the full length MIP. Separation is optional.

Chemical synthesis of oligos often results in a mixture of products of varying lengths. For example, when the oligo synthesis method is 3' to 5' the resulting products typically include product that is missing one or more bases at the 5' end, for example, if the full length oligo is 20 bases there will be some oligos in the mixture that are 19, 18, 17 etc. representing products that did not complete synthesis. When forming MIPs using the ligation method described above, truncated B oligos do not efficiently ligate to the F oligo because the truncation at the 5' end results in a gap between the ends of the F and B oligo of one or more bases. Similarly, 5' truncated F oligos do not ligate efficiently to the A oligo because of the gap between the ends.

For each MIP to be synthesized, a ligation reaction is set up combining a pre-annealed F and C complex with the A oligo for that MIP and the B oligo for that MIP. The ratio of A/B may be about 1:1. Lower amounts of F and C can be used. In one embodiment A/B/F/C is 5:5:1.2:1 in 50 µl. Other combinations may be used as well. For example, 15:15:3:3.6 in 60 µl or 15/15/6/7.2 in 70 µl or 15/15:9:10.8 in 70 µl or 15:15:12:14.4 in 70 µl.

After ligation the MIPs can be pooled and the products separated by denaturing gel electrophoresis to enrich for the full length MIP. The desired products that have A ligated to F ligated to B are the longest products. Smaller products representing A ligated only to F or F ligated only to B migrate at a distinct location from the AFB product. The portion of the gel that contains AFB can be cut out and separated from the rest of the gel and then the nucleic acid can be eluted from the gel slice. In an alternative embodiment an affinity selection step may be used.

Figure 2:
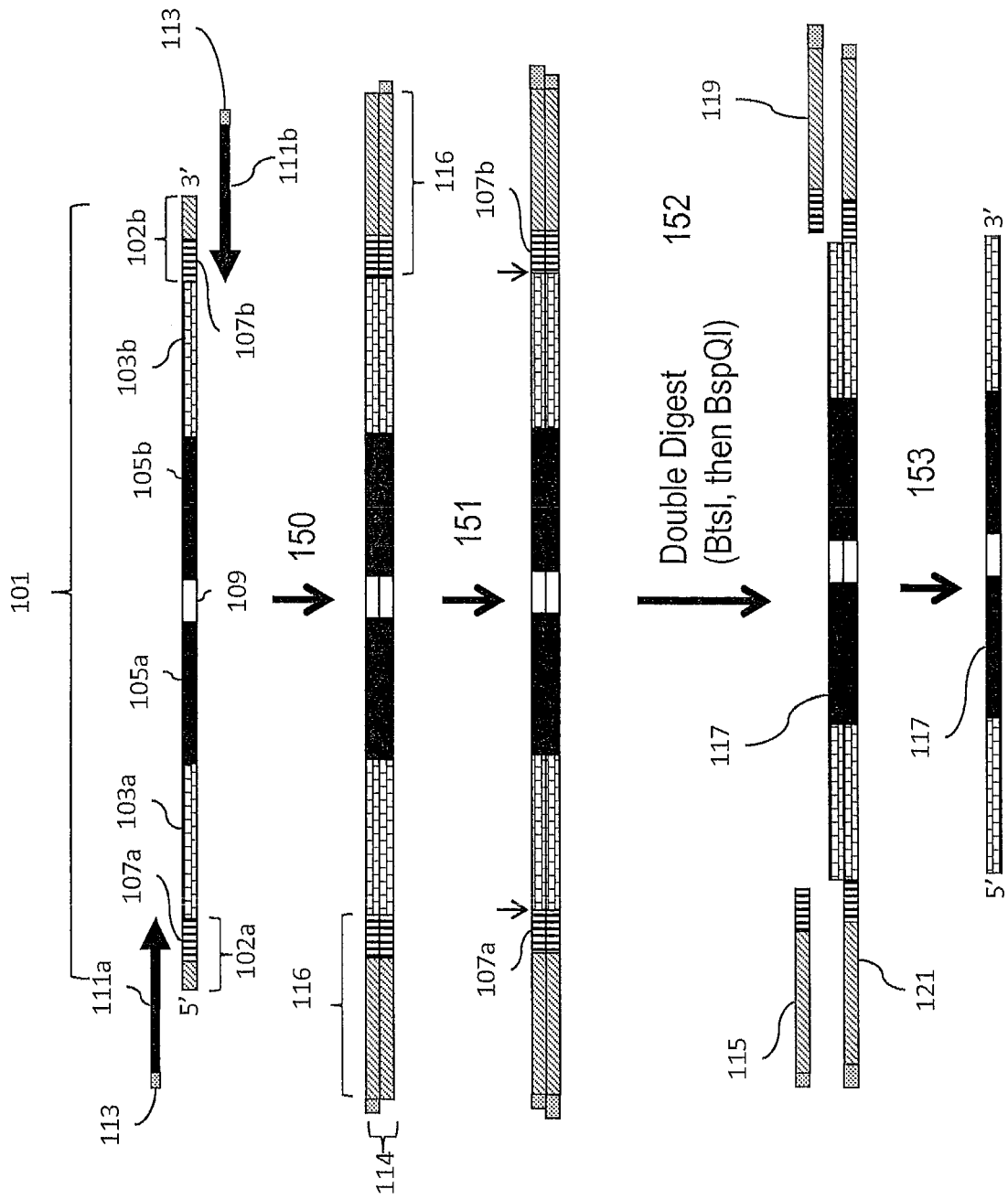
FIG. 2 shows a method for preparation of pools of MIPs using a precursor probe with incorporated nicking sites.

In another aspect the MIPs are prepared by a method that does not include a ligation step. This method is shown in FIG. 2. For each MIP a small amount of a precursor probe 101 is synthesized chemically. A large number of different precursors can be synthesized in small amounts and pooled into a single volume of liquid prior to a first amplification step. The precursor probes 101 contain the entire MIP (including first homology region 103a, universal analytical priming site 105a, cleavage site 109, universal analytical priming site 105b and second homology region 103b, collectively 117) flanked by regions 102a and 102b. Regions 102a and 102b served as binding sites for the preparative universal primers in the first round of primer extension. The final probe 117 does not include the regions 102a and 102b.

The precursor probes are processed into MIPs as shown in FIG. 2. Regions 102a and 102b include the recognition sequence 107a and 107b for the nicking enzymes that will be used to separate the MIP 117 from the amplification product. Universal preparative primers 111a and 111b are used to amplify the precursor probes. The preparative primer have 5' overhanging regions relative to the precursor regions 102a and 102b so the double stranded precursor PCR product 114 includes regions 116 that will not be included in the final MIP. The cleavage site 109 is preferably a recognition sequence for a restriction enzyme, for example, NotI. First and second preparative primers 111a and 111b are shown by arrows and have a biotin label 113 at the 5' ends. In one embodiment, the first nicking site 107a is for BspQI and the second nicking site 107b is for BtsI, both enzymes are available as nicking variants from New England Biolabs. In one aspect primer binding sites are selected to contain recognition sites for a nicking enzyme. In one aspect a type IIs nicking enzyme may be used, e.g. N.Alw I and/or N.BstNB I (also available from New England Biolabs). Other nicking enzymes that may be used include, for example, Nb. Bsm I, N. BbvC IA and N. BbvC IB. In another aspect the primers may be engineered to contain a restriction enzyme recognition site and the site in the primer is blocked from cleavage, for example, by incorporation of a thiol linkage. After capture and washing, single stranded polynucleotide may be release by treating with such nicking enzymes, after which it may be purified from the reaction mixture and solid phase supports by conventional means, e.g. preparative gel electrophoresis. For polynucleotides being used as circularizing probes, 5' phosphate groups may be added enzymatically using a conventional kinase reaction.

```
Nt.BspQI recognizes the following site:
5' GCTCTTCN/

3' CGAGAAGN

Nb.BtsI recognizes the following site:
5' GCAGTGN

3' CGTCAC/N
```

The full length processed probe is designed such that the first base of the probe is immediately 3' of the cleavage site for the Nt.BspQI site and the last base of the probe is immediately 5' of the cleavage site for the Nt. BspQI site as shown below:

```
                                              (SEQ ID NO. 9)
5' GCTCTTCN▼PROCESSED_PROBE▼CACTGC 3'

3' CGAGAAGN NNNNNNNNNNNNNNNNN GTGACG 5'
```

Step 150 includes amplification of the precursor. In one aspect amplification is by PCR with 5' biotin preparative primers 111a and 111b. After Exo-SAP (Affymetrix) cleanup the 3' ends of the strands in double stranded PCR product 114 may be end labeled in step 151 with biotin using terminal transferase to incorporate a biotinylated nucleotide such as DLR (Affymetrix). This results in biotin labels at the 5' and 3' ends of both strands of the double stranded PCR product 114. The product is then subjected to digestion in step 152 with both nicking enzymes so that the upper strand is cleaved at sites 107a and 107b as shown. Any enzyme or enzyme combination that results in cleavage of that top strand at the positions indicated by the small arrows can be used. In preferred aspects the top strand is cleaved in step 152 at the boundary between the cleavage site 107a/107b and the target recognition portions 103a/103b of the MIP. This position is shown by small arrows in the product of step 151 in FIG. 2. This cuts the top strand into three distinct pieces, a 5' region 115 that includes the preparative priming region, the central MIP region and nicking recognition site 117 and a 3' preparative priming region 119. The bottom strand 121 is left intact. Products 115, 119 and 121 are biotinylated at one or both ends. Product 117 is not biotinylated and this difference may be used to separate the MIP product 117 from the by-products 115, 119 and 121 in step 153. For example, the products can be denatured and affinity selection can be used to pull down the biotinylated products from the unbiotinylated products. There may also be some intermediates that result from failure of one or the other enzyme to cleave (115+117 or 117+119) and some that fail to cleave at both nicking sites. These intermediates will be biotinylated at least on one end. The desired full length probe can also be separated from the intermediates by size selection. For example electrophoretic gel separation may be used. Biotin is an exemplary hapten but other haptens are available and may be used.

Figure 3A:
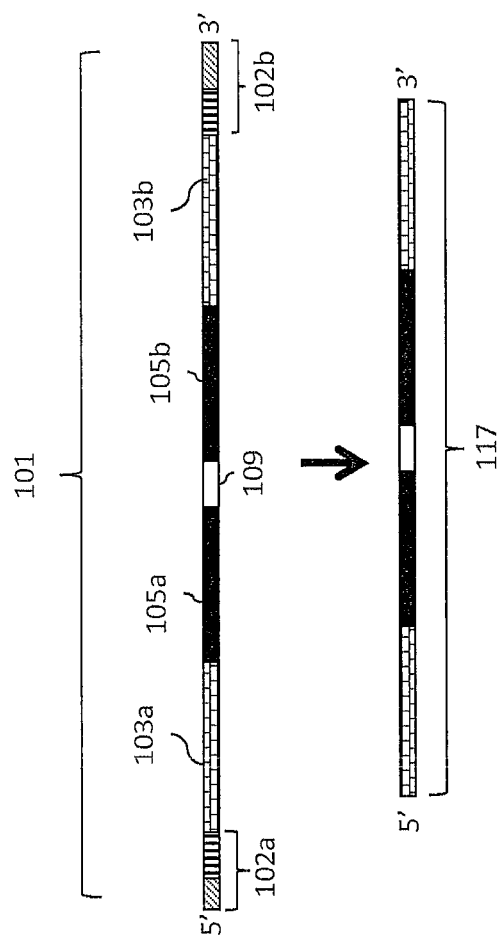
FIG. 3A shows a precursor MIP and MIP, both without a tag sequence.
Figure 3B:
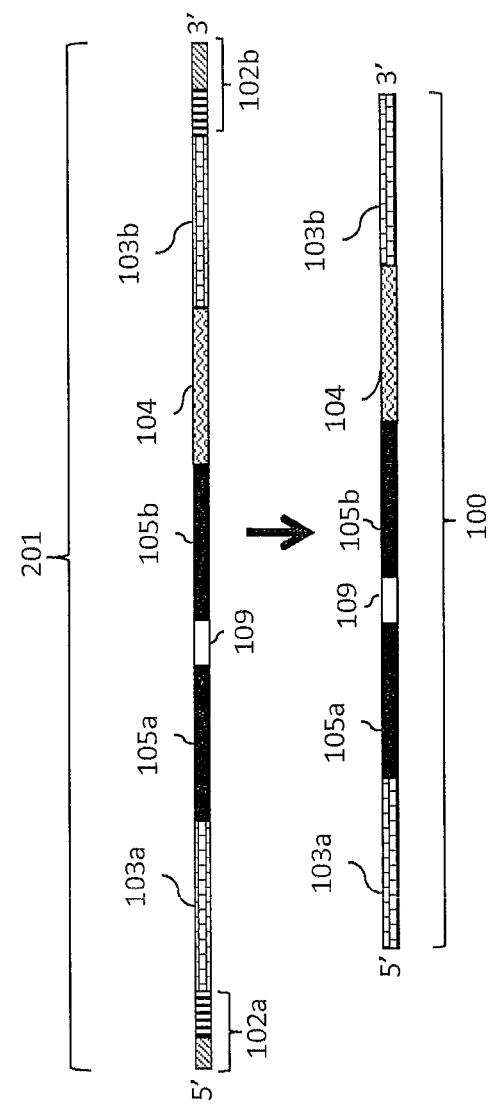
FIG. 3B shows a precursor MIP and MIP, both with a tag sequence.

In some aspects the precursor probe and the resulting MIP probe may have additional features, for example, a tag sequence may be included. FIGS. 3A and 3B show the precursor MIPs 101 and 201 and the MIP products 117 and 100 without a tag FIG. 3A or with a tag FIG. 3B. The tag sequence 104 is included in the precursor probe 201 between the 3' analytical primer 105b and the 3' target homology region 103b. In comparison to the pre-MIP without tag 101 and the MIP without tag 117 as shown in FIG. 3A, the pre-MIP 201 and MIP 100 with tag have an extra sequence indicated by 104, preferably 20 to 25 bases, that can be used as a tag sequence for downstream analysis in the MIP assay as previously described in, for example, U.S. Pat. No. 6,858,412, which is incorporated herein by reference in its entirety for all purposes.

The MIPs made using the precursor probe methods are amplification products and thus lack the uracils that can be included in the ligation method shown in FIG. 1B. When using the ligation method the oligos that form the MIP are chemically synthesized and can easily be synthesized with uracils in the cleavage site in the central oligo identified as 106c in FIG. 1B. Because MIPs are single stranded during the hybridization and circularization steps of the assay the cleavage site within the closed circle is also single stranded. As shown in FIG. 4, to facilitate cleavage at a site that must be double stranded for cleavage, a short single stranded oligo 301 can be hybridized to the MIP to create a double stranded region that can be cleaved by a restriction enzyme, for example a type II restriction enzyme or a type IIs enzyme. In another aspect the oligo can introduce a G:A mismatch which can be recognized by MutY glycosylase and AP endonucleases such as EndoIV. MutY glycosylase removes the mispaired A and the abasic site is nicked by the AP endonucleases as described in Howell et al. *NAR* (2010): 38(7) e99 which is incorporated herein by reference.

```
An exemplary pre-MIP sequence may be
                                      (SEQ ID NO. 1)
5' AGGACCAGCT CTTCTAAGTC GTGAGCTTGC AGCTTCTTCA

GCTTCCCGAT TACGGCGGCC GCACGATCCG ACGGTAGTGT

GCAGGCTGTC ATTACTCCAC CACTGCGTGA ACTGA 3'
``` where the underlined sequences correspond to the first and second preparative universal primer regions, the bold regions are the genomic homology regions H1 and H2, the italicized region is the Not I cleavage site and the rest is the analytical primer regions. The nicking enzyme recognition sites are 5' GCTCTTCN▼ 3' for Nb. BspQ1 with the enzyme cleaving after the 3' N as indicated by the "▼" and 5'NN▼CACTGC 3' with the enzyme cleaving between the N and the C for Nb. BtsI as indicated. This example does not include a tag sequence, but in preferred aspects a tag may be included between the second analytical priming site and the H2 region. The universal priming regions including the nicking enzyme recognitions sites may be about 15 bases each, the genomic homology sites (H1 and H2) may be about 20 bases, the analytical universal priming sites may be about 20 each and may include the entire cleavage site or some portion thereof. The tag region may be between 15 and 25 bases and in many embodiments is 21 bases. In some aspects there may be another cleavage site, e.g. a restriction enzyme recognition site between the tag 203 and the second homology region 103b.

The different populations can also be separated by electrophoretic size separation. The MIPs are smaller than the precursor MIPs, the complementary strand and either single cleavage product and larger than the cleaved preparative primer regions.

In a preferred embodiment precursor probes are chemically synthesized in small amounts, for example, 20 ng of each precursor oligonucleotide in 25 µl of water, the amount may be, for example, in the range of 1 to 100 ng and the concentration may be in the range of 0.1 to 2 ng of oligonucleotide per µl of water. The precursor may be synthesized as a single strand that includes the desired probe flanked by a first priming region at the 5' end and a second priming region at the 3' end. The first priming region includes a first nicking enzyme recognition site sequence and the second priming region includes a second nicking enzyme recognition site sequence. The precursor oligonucleotide will be longer than the final probe design by the length of at least the flanking priming regions. For example, if the final probe is to be 85 nucleotides and each priming sequence (including nicking site) is 15 bases then the total will be 85+15+15=115 bases.

The precursor oligonucleotides are synthesized, for example, in an array format so that individual sequences are synthesized in parallel in a feature or area so that each feature or area contains many copies of the same sequence and neighboring features contain different sequences, although the features may overlap or multiple sequences can be synthesized in a single feature. The precursor oligos are then separated from the support, for example, by cleavage, and pooled. The pool may contain 100-500, 500-1000, 1000-3000, 3000 to 10,000, 10,000 to 100,000 different precursor oligonucleotide sequences. After pooling, the precursor oligonucleotides, which are single stranded, are used as template in a PCR. A primer complementary to the second preparatory universal priming region is hybridized to the oligos and extended to make a first copy of the precursor oligo. The now double stranded precursor can be amplified by PCR using the preparatory universal priming sites. In a preferred aspect, both universal primers may modified with an affinity selectable group, for example, they may be biotinylated at the 5' end for later affinity selection.

After the preparative PCR the double stranded products may be treated with terminal transferase to add a biotin labeled nucleotide to the 3' ends of the strands, resulting in double stranded products with each of the ends (both 3' ends and both 5' ends) having an affinity selectable reagent such as biotin. All ends may have the same affinity selectable reagent or two or more different affinity selectable reagents may be used. The 5' ends may also be labeled by using biotinylated primers for PCR.

After labeling of the 3' ends the double stranded product may be subjected to cleavage with the nicking enzymes that recognize the nicking enzyme recognition sites in the first and second preparative universal priming regions. The sites are arranged so that both cleave within the same strand and do not cleave the opposite strand.

Synthesis of oligonucleotides in microarray formats using photolithography as been previously described. See, for example, Fodor et al. *Science* 251(4995), 767-73, 1991, Fodor et al., *Nature* 364(6437), 555-6, 1993 and Pease et al. *PNAS* 91(11), 5022-6, 1994. The lengths of the precursor probes in the pool are preferably between 100 and 150 bases. The length of individual probes within the pool may vary. For example, there may be some precursor probes that are 110 bases and some that are 130 within the same pool. In one aspect a pool was designed with precursors of the following lengths: 110, 116, 119, 121 and 123 bases. The length may vary depending on desired lengths of H1, H2, and the tag sequence. In some aspects tags are excluded and the probes are shorter. The tags may be, for example, 21 to 25 bases. The H1 region may be, for example, 18 to 30 bases, the H2 region may be, for example, 17 to 32 bases. The central universal priming region may be about 34 to 60 bases. Pools of synthesized oligonucleotides of length 100 to 150 or longer are commercially available from, for example, LC Biosciences. See Tian et al. (2004) *Nature* 432, 1050-1054 and Zhou et al. (2004) *Nucleic Acids Res.* 32, 5409-5417. Pooled oligonucleotides for use in multiplexing reactions can be synthesized in batches of thousands of oligonucleotide synthesized in parallel and then cleaved into solution in a single microtube. Synthesis may be via standard DMT chemistry so that stepwise yield is high, resulting in a high quality final product with oligos up to 200 bases in length or longer. The product is delivered as a pool in a single microtube.

The MIPs synthesized using an amplification method differ from MIPs formed of chemically synthesized oligonucleotides at the cleavage site. When probes are chemically synthesized it is easier to incorporate modified bases such as uracils at the cleavage site. This is more difficult when the probe is being synthesized enzymatically as in many of the methods disclosed herein. It is possible to incorporate modified bases in enzymatically synthesized products, for example, the modified bases can be in the chemically synthesized primers or they can be incorporated by the enzyme, but it is more difficult to specify the location of incorporation. When the MIP is chemically synthesized the cleavage site 109 can be one or more uracil bases. This facilitates single strand cleavage using UDG in combination with cleavage at abasic sites, for example an AP endonucleases. In probes that are enzymatically synthesized a restriction site may be included at cleavage site 109.

Although, the synthesis of MIPs is used to illustrate the methods disclosed herein they can also be used to synthesize and amplify a variety of oligonucleotide pools or libraries. The lengths of the oligos that can be generated using the method are limited by the length of the precursor oligo that can be made. Currently commercial oligos up to about 200 bases can be made in large pools. The methods disclosed herein can be applied to PCR amplification of virtually any pool or library of oligos.

Figure 5A:
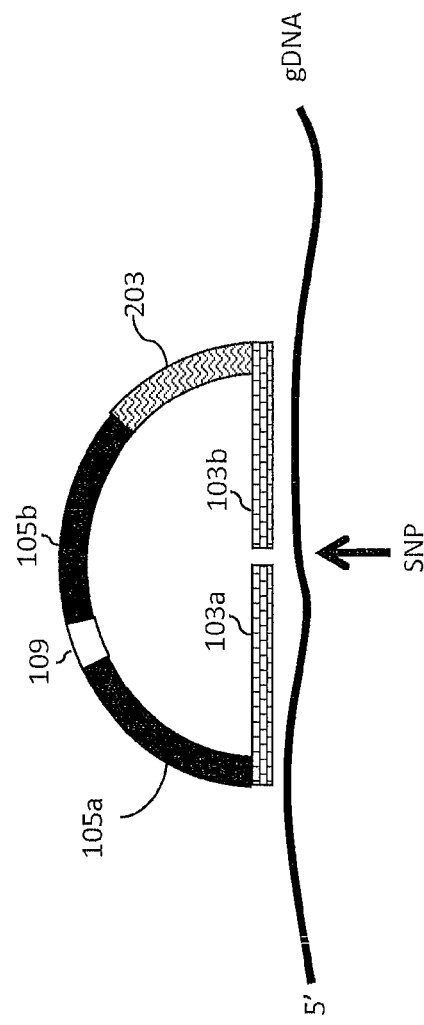
FIG. 5A shows a MIP hybridized to a target with a SNP location shown in the gap between the ends of the probe.
Figure 5B:
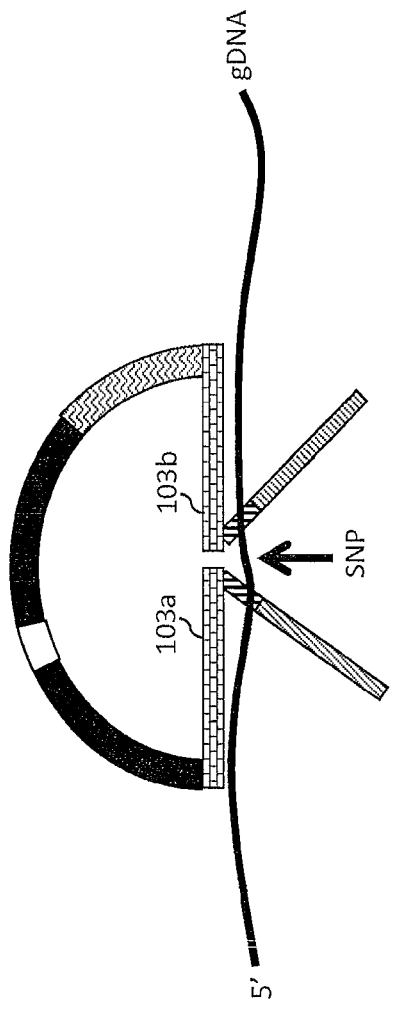
FIG. 5B shows a schematic of the precursor MIP oligo in relation to the target.

FIG. 5A shows the MIP hybridized to a gDNA target with a SNP at the junction between H1 and H2. FIG. 5B shows for illustration purposes how a precursor-MIP would hybridize to the same target with overhangs that include the priming sites and the nicking sites if the preparative priming sites were not removed. The structure in FIG. 5B does not allow for ligation of 103a to 103b to form the closed circle structure without removal of the overhanging ends.

FIG. 6 illustrates another method for synthesis of MIPs. Two separate oligos are synthesized for each MIP. The first oligo has a 5' common primer region 115, H1 region 103a, common primer region 105a, cleavage site 109, common primer region 105b and tag region 104. The second primer has common priming region 119, H2' region 103b', optional second cleavage site 109b and tag complement 104'. Regions 104 and 104' are complementary so that the two oligos hybridize and form a duplex in that region as shown. The 3' ends of both oligos are then extended in step 650 using DNA polymerase. The top strand oligo serves as template for the bottom strand oligo extension and the bottom strand oligo serves as template for the extension of the top strand oligo. The resulting extension product is a double stranded full length MIP flanked by priming sites 115 and 119. The product can be amplified in step 651 by PCR or any other amplification method. The universal priming regions 115 and 119 can be cleaved in step 652, for example, by restriction digestion if restriction sites are included in the priming sites, to separate the priming regions from the double stranded MIP. The sites should be designed so that they cleave so that the ends of the 103a and 103b regions are at the ends of the MIP. The MIP can be separated from its complement in step 653.

In another aspect the precursors used in this method need not have the universal priming regions 115 and 119. The precursor templates may end with the H1 and H2 regions 103a and 103b. As described above two oligonucleotides are synthesized for each MIP to be generated. The oligos have a region of complementarity at the 3' ends so that the 3' ends of the members of a pair form a double stranded duplex and each can serve as template for the extension of the other as shown in FIG. 6. When the universal priming regions are omitted the extension product is simply the double stranded. MIP. Amplification can be omitted. If amplification is omitted the amount of product possible is limited to the amount of input synthesized precursor. A benefit of this approach is that both oligos are shorter than the full length final product and it is generally simpler and less expensive to synthesize shorter oligos synthetically. The region where the upper strand oligo and the lower strand oligo are complementary sis preferably a region that is unique to each MIP to be generated, for example the tag region 104 or the H2 region 103b in FIG. 6. This allows for multiple pairs to be mixed in a single reaction for extension because only the cognate members of a pair will be complementary in that region. Alternatively single pairs can be hybridized and extended in separate reactions and subsequently pooled. If the oligo pairs are to be extended in separate reactions the complementary region can be a common region such as region 105b in FIG. 6.

Figure 7:
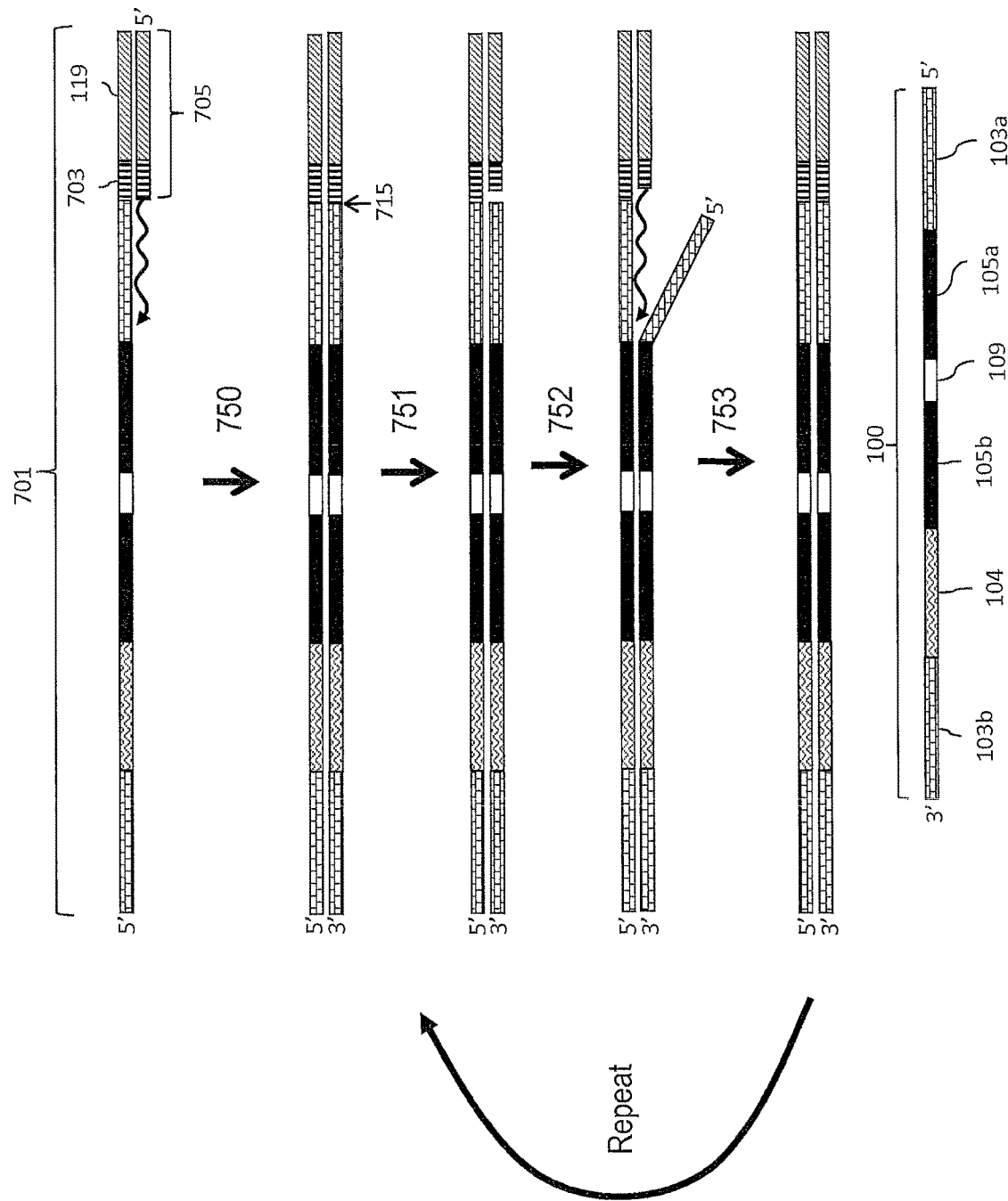
FIG. 7 shows a schematic of a method for synthesis of oligonucleotides by linear amplification from a precursor using a regenerating primer.

FIG. 7 shows another method for generating MIPs. A precursor template MIP 701 is synthesized. The precursor template has the complement of the MIP, a cleavage site 703 and a universal priming site 119. An oligo 705 that is complementary to the priming site and the cleavage site is hybridized to the precursor template and extended in step 750. The extended portion will be the MIP. The now double stranded product is cleaved in step 751 at the cleavage site 703 to generate a nick in the lower strand at or near the position indicated by arrow 715. The upper strand is not cleaved. The primer region can be extended again in steps 752 and 753, displacing the lower strand. The displaced lower strand is the MIP 100. The product of extension is the double stranded product that is the starting material for step 751. The cleavage and extension can be repeated to make multiple copies of the desired probe. The cleavage site 703 is regenerated each time. In another aspect the primer can be digested following extension to generate the 5' end of the MIP. This may be, for example, by using an RNA primer or an RNA/DNA chimeric primer and treating the product with RNase H after extension. The extension of the RNA primer using a DNA polymerase and on a DNA template creates an RNA-DNA hybrid. The RNA in that hybrid can be cleaved by RNaseH generating a single stranded region where a new RNA primer can hybridize and extended. Preferably the RNA is 5' of the DNA portion of the chimeric primer. This reaction can be isothermal. The extension of the RNA primer displaces the probe. Related methods of using an RNA primer or a composite RNA-DNA chimeric primer are discussed, for example, in U.S. Pat. No. 6,946,251 Kurn et al., which is incorporated herein by reference in its entirety for all purposes, but specifically for methods related to this amplification method.

The nicking site 715 can be a recognition site for a nicking enzyme. Other methods for generating a nick for primer extension and strand displacement amplification are disclosed in US Patent Pub 20090117573 the entire disclosure of which is incorporated herein by reference in its entirety. See also U.S. Patent Pub 20040115644, which is incorporated herein by reference in its entirety.

Precursor templates are synthesized for the MIPs to be included in the pool. These can be made at a small scale thereby reducing cost. The 3' end of the precursor templates are synthesized with a universal priming site at the 3' end. A primer is annealed to this site and a run off polymerization is performed to create many copies of a single stranded target that is the complement of precursor template at the region upstream of the universal priming site. This region corresponds to the complete MIP. This run off could be generated using a variety of polymerases. For example, a DNA dependent RNA polymerase such as T7 RNA polymerase could be used or a DNA dependent DNA polymerase such as Phi29, Bst, Klenow or Taq polymerases. In some aspects the polymerase preferably has strand displacing activity so that subsequent rounds of polymerization displace previously made copies of the MIP. If an RNA polymerase is to be used the primer region preferably includes an RNA polymerase promoter sequence. A complementary oligo can be hybridized to this to form a double stranded promoter region. The complementary oligo may be blocked from extension. The resulting RNA could be converted to DNA in a subsequent step.

In another aspect, a nicking and polymerization type scheme or standard linear amplification may be employed. A cleavable linkage may be included between the primer and the desired final MIP sequence to be generated. This linkage could be an RNA nucleotide or some other linkage that has the properties of being cleavable but preferably such that the site is regenerated after extension so cleavage and extension can be repeated multiple times. Cleaving at the linkage separates the MIP from the primer region. In one aspect the primer may be labeled with a first hapten and the extension product with a second hapten. Haptens that may be used include, for example, biotin or fluorescein. An affinity pull down for the second hapten can be used to separate (for example, biotin or fluorescein) and a second hapten is incorporated in the extension product. A selection scheme may be used to separate the full length probes from the precursor material and the primers. In one aspect a positive selection can be used to pull out sequences that have the second hapten and a negative selection scheme may be used to deplete primers and non-cleaved extension products. Haptens that may be used include, for example, digoxigenin (DIG), dinitrophenol (DNP), biotin and fluorescein and derivatives thereof. Anti-hapten antibodies for each of these haptens are commercially available.

In other aspects some of the intermediates can be removed by selective digestion. For example, selective exonuclease digestion of the strand of the double stranded intermediate that does not contain the processed probe can be used.

Another method for amplifying probes is shown in FIG. 8. As in FIG. 2, a precursor probe 800 that includes the full length probe flanked by precursor amplification regions is synthesized chemically. The precursor has a region 102b that includes a recognition site for a restriction enzyme 803, preferably a type IIs restriction enzyme. The region 102b serves as a binding site for a universal preparative primer 111b. The primer is hybridized and extended. A second universal primer 111a that is biotinylated at the 5' end and contains 1 or more U bases at or near the 3' end is then hybridized to the extension product and extended. As one of skill in the art will appreciate, the precursor probe template can either be synthesized initially as the top strand (5' to 3' left to right in the figure) or as the bottom strand (3' to 5' left to right in the figure). The orientation in which the precursor template is synthesized will determine which primer binds to the synthetic strand to generate the first strand cDNA. The order of binding and extension is determined by the orientation of the precursor. The resulting double stranded product is amplified by PCR using the same universal preparative primers 111a and 111b. The product of the amplification step 850 is a double stranded precursor 814 that has cleavage site 801 comprising 1 or more U bases in the top strand and cleavage site 803 comprising a type IIs recognition site. The top strand is biotinylated at the 5' end 113. The fragment is digested in step 851 with the type IIs enzyme to cleave at the site 815 indicated with arrows. This cleavage creates the 3' end of the MIP and separates precursor 816 from the universal priming region 817. In step 852 the top strand 818 of 816 is separated from the bottom strand and from 817 by affinity selection using the biotinylated end 113 for affinity selection. In step 853 the product 818 is cleaved at cleavage site 801 using UDG treatment followed by cleavage so that the 5' end of the MIP is generated at location 820. The product of step 853 is the full length MIP 100.

When generating large pools of probes, such as MIPs, and amplifying to generate material for multiple samples it may be desirable to knock out the function of some of the probes under some conditions. For example, if a pool of about 300,000 different MIPs is generated and amplified using the methods disclosed herein, it may be discovered at a later time that some of the probes in the pool interfere with other probes or are directed to regions that are not of interest. Rather than remaking the pool it may be desirable to mitigate the interference of a subset of the probes or to reduce or eliminate the function of those probes within the pool but continue to use the pool. You may for example want to "kill" 1 to 10 or 10 to 100 or more than 100 probes in a pool but only for the purpose of processing a particular set of samples. Alternatively you may want to "kill" 1 or more probes in the entire pool.

In some aspects the tag for each MIP in a pool is unique to that MIP and specific for the target to which the MIP is directed. Pools of unique tags have been previously described. A greedy algorithm may be used to generate tags. A pool of all possible sequences of a give length can be the starting material. For example, all possible 23 mers ($7 \times 10^{13}$). The algorithm may test each 1 by 1 for the following: (1) GC content of 8-10 out of 23, less than 4 out of 5 and less than 7 out of 12; (2) Tm of 58.5+/−2 degrees; (3) unique 12-mers as compared to a list of used 12 mers; (4) no predicted cross hybridization greater than a selected threshold when compared to others in the selected "good" set; and (5) self-folding Tm below a selected threshold. If a tag passes these tests add it to the "good" set and add the 12 mers to the group of "used" 12 mers. The unique N-mer length can be decreased for smaller tag sets, for example, 11 for 100,000 tags, 12 for 400,000 and 13 for 1,600,000.

In one aspect, pools of probes can be treated to eliminate the function of some probes in the pool that are not of interest in a particular assay. For example, a pool may contain one or a few probes that are not of interest and those probes can be blocked from generating a result by hybridizing an oligo to some region of the undesired probes. The oligo can hybridized, for example, to part of the tag region and to part of the H2 region of a targeted MIP. The probe may be, for example, 43 bases and hybridized to the entire tag region (25 bases), 5 bases upstream of the tag region and 13 bases downstream of the tag region (including part of H2). This "probe kill" method prevents binding of interfering probes in a pool. The probes may be "interfering" for example, if they are targeted to a region that is near another region of interest, for example, the H1 or H2 binding sites of the "interfering" probe may overlap with the probe of interest. In another aspect a shorter kill probe can be used so long as it is specific for the MIP that is being targeted. To facilitate shorter kill probes oligos with higher binding affinities may be used. For example, the kill probes may have one or more conformationally restricted oligonucleotide analogs, such as locked nucleic acid linkages (LNAs), constrained ethyl and other bicyclic and tricyclic nucleoside analogues as described in U.S. Pat. Nos. 6,268,490, 7,572, 582 and 7,666,854, and as reviewed in Orum and Wengel, *Curr. Opin. Mol. Ther.* 2001, 3(3):239-43, each of which is incorporated herein by reference in its entirety. The conformational and steric hindrance of these molecules results in an increased thermal stability of duplexes formed between oligonucleotides containing these analogues and complementary DNA or RNA.

Pools of MIPs can be synthesized, according to the disclosed methods, to analyze targets in selected subgroups of genes, transcripts or chromosomal regions. For example, a set of probes can be synthesized to analyze targets that have been implicated in cancer or cytogenetic markers. The MIP assay is particularly amenable to analysis of samples derived from FFPE samples. The assay targets regions that are relatively short, 30 to 60 bases for example, compared to other methods that amplify the sample, for example by PCR, prior to analysis. Multiple MIPs can be directed at a single gene target, each detecting a different region of the target. This provides for multiple independent data points for a given gene target. The MIP assay can be used to provide genotypes for the targets, facilitating analysis of loss of heterozygosity and allele-specific aberrations.

In another aspect the pools of probes that are prepared according to the methods disclosed are probes to be used to capture target sequences for further analysis. See for example Porreca et al. *Nat Methods* (2007) 4(11):931-6. In other aspects the pools of probes are used for analysis of methylation. Other applications of padlock probe technology to which the present methods may be applied have been disclosed, for example, Li et al. *Science* (2009) 324:1210-1213 and Li et al. *Genome Res* (2009) 19(9):1606-1615.

It is understood that cancers are caused by the accumulation of genomic alterations. Analyses of cancer genome sequences and structures provide insights for understanding cancer biology, diagnosis and therapy. For a review see, Meyerson et al. Nat. Rev. Genet. 11, 685-696 (2010). The methods and compositions disclosed herein can be used to obtain increased efficiency and resolution of detection of each of the principal types of somatic cancer genome alterations, including nucleotide substitutions, small insertions and deletions, copy number alterations, chromosomal rearrangements and microbial infections. The methods and compositions of matter disclosed herein may be used for characterizing somatic genome alterations in cancer through whole-genome, whole-exome and whole-transcriptome approaches and thereby facilitating advanced in cancer genomics.

Pools of probes that may be generated using the disclosed methods may target a large number of different analytes of interest and can be customized for almost any application. For example, the pools may be probes for a plurality of exons in a genome, for a plurality of promoter regions, for imprinted genes, for cancer markers, both DNA copy number and gene expression, microRNAs, miRNAs, siRNAs, viral markers, infectious disease markers, pluralities of targets in agriculturally important organisms, e.g. bovine, porcine, chicken, rice, or research organisms e.g. zebra fish, yeast, rat, mouse. Use of the MIP assay for detection of RNA templates has been disclosed, for example, in US Pat. Pub. 20100184618. The homology regions are designed to flank the region of interest and the 3' end is extended through the region of interest and ligated to the 5' end of the probe prior to amplification. The amplified product can be analyzed by any available method, for example, sequencing. In some aspects algorithms and software products that are designed to optimize the design of pools of probes to minimize cross reactivity are also contemplated.

Kits may include, for example, precursor probes, one or more primers, a DNA polymerase, one or more restriction enzymes that may be nicking enzymes, UDG or an AP endonucleases. Buffer mixtures and nucleotides may be included as well. In some aspects primers in the kit may have an affinity reagent attached, such as a biotin or another hapten, or may include one or more uracils or modified nucleotides such as an LNA or inosine.

In another aspect the closed circular probes are amplified without cleavage to open the circle. A strand displacing polymerase such as phi29 DNA polymerase may be used to perform a rolling circle amplification (RCA) as described, for example, in Margeridon et al. Antimicrobial Agents and Chemotherapy 52(9):3068-3073 (2008), Zhang et al, *Mol. Diagn.* 6:141-150 (2001), Fire and Xu, *PNAS* 92:4641 (1995) and Liu et al., *J. Am. Chem. Soc.* 118:1587 (1996)). The phage phi29 enzyme is particularly useful for RCA because it has a strong 3' exonuclease (proofreading) activity, has strand displacing activity and is very processive so it can polymerize more than 70,000 nucleotides without detaching from the template (see, Blanco et al. *J. Biol. Chem.* 264:8935-8940 (1989). This RCA step, which is high yield, may replace the PCR amplification step or steps. In some aspects an RCA step may be followed by PCR. Preferably the RCA is primed using specific primers that are designed to be complementary to a region on the MIPs, but random primers may also be used. If amplification is by RCA alone there is no need for the primer pair as a single priming site may be used. If, for example, there is a single common priming site of the MIPs the primer that is complementary to that priming site can be used to primer RCA. The product in theory is a long single stranded primer extension product having many contiguous copies of the complement of the closed circle. To generate double stranded copies of that extension product or portions thereof, a second primer or primers can be used. The second primer may be the complement of the first or it may be complementary to another priming site in the expected extension product. Alternatively, random primers may be used for second strand synthesis. Kits for performing phi29 amplification are commercially available, for example, the SEQ-TEMPLIGEN™ RCA kit available from Solgent, Inc. GENOMIPHI™ and TEMPLIPHI™ kits from GE Healthcare may also be used.

The resulting double stranded products can be cleaved into defined fragments by the use of a restriction enzyme, for example, HaeIII. HaeIII is known to work well on MIP amplification products and the GGCC recognition site has been screened against genomic sequence in the design of the current MIP panels so it is the preferred enzyme, but other enzymes could also be used. Preferred enzymes will be robust cleavers that function well in the buffer conditions used for RCA. The restriction digestion may be used to cut the long amplification products into fragments that are approximately the size of the starting probes, for example, about 120 base pairs. The second site may be between the tag and the genomic homology region so a cleavage product containing the tag and primer is released for hybridization to the array probes.

In some aspects the methods disclosed herein are useful in combination with the methods and products disclosed in U.S. Pat. No. 7,745,091, which is incorporated herein in its entirety. In many aspects, probe pools that are amplified using the methods disclosed can be attached to encoded microparticles or used in assays that employ microparticles. Methods for making microparticles are disclosed, for example, in U.S. Pat. No. 7,745,092 which is also incorporated herein by reference. Other related methods that can be used in combination with the disclosed methods are described in U.S. Patent Pub 20090004701 and 20080293589 and in application Ser. No. 12/969,581 which are also incorporated herein by reference.

In another aspect molecular inversion probe methods are combined with stochastic labeling methods as disclosed in US Pat. Pub. 20110160078 and Fu et al. *Proc Natl Acad Sci U.S.A.* 108(22):9026-31 (2011), both of which are incorporated herein by reference in their entireties. For example, closed circular probes can be formed as previously described (see U.S. Pat. Nos. 6,858,412 and 7,700,323, both incorporated by reference in their entireties) and then linearized after exonuclease digestion of uncircularized fragments as previously described (see FIG. 9A). Briefly, target homology regions 1116 and 1118 flank the un-inverted probe. The probe also contains priming regions 1102 and 1106, optionally cleavage region 1104 and tag region 1110. Spacer regions 1108 and 1114 may also be included and may contain optional features such as additional priming regions and restriction sites, for example. The un-inverted probe hybridizes to target 1100 leaving a gap 1120. The gap may be one or more bases or it may simply be simply a strand break. The gap is closed 1124 thereby forming a circular molecule as shown in the middle illustration on the left side of the figure. The circle may be cleaved at 1104, but this is optional. The resulting "inverted" probe 1128 has a first universal priming site 1102 at the 5' end and a second universal priming site 1106 at the 3' end. The universal priming sites flank first and second target specific regions and optionally a tag sequence. Primers 1132 and 1134 may be used to amplify the inverted probes to make amplification product 1136.

Figure 9A:
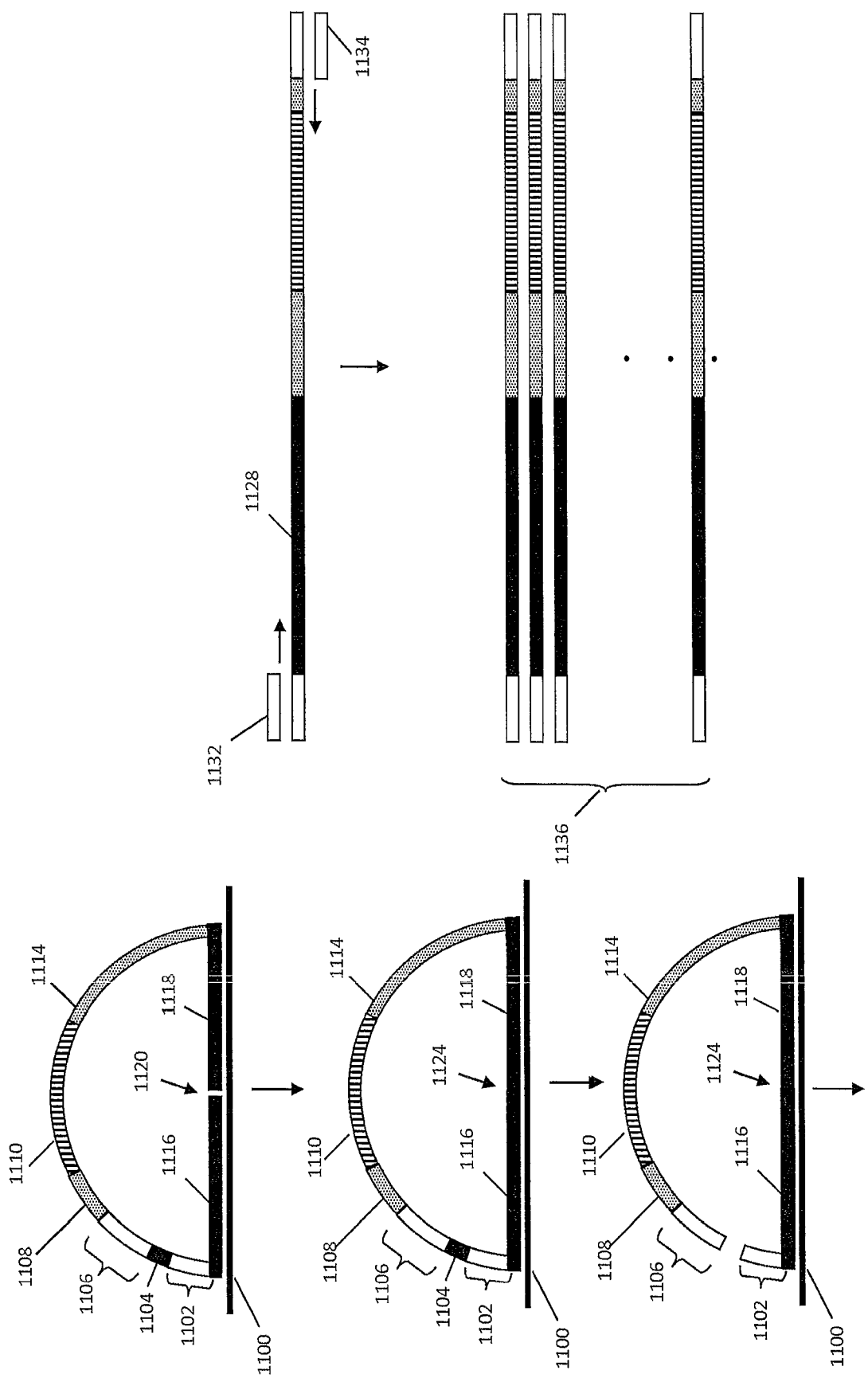
FIG. 9A shows a schematic of the molecular inversion probe method.
Figure 9C:
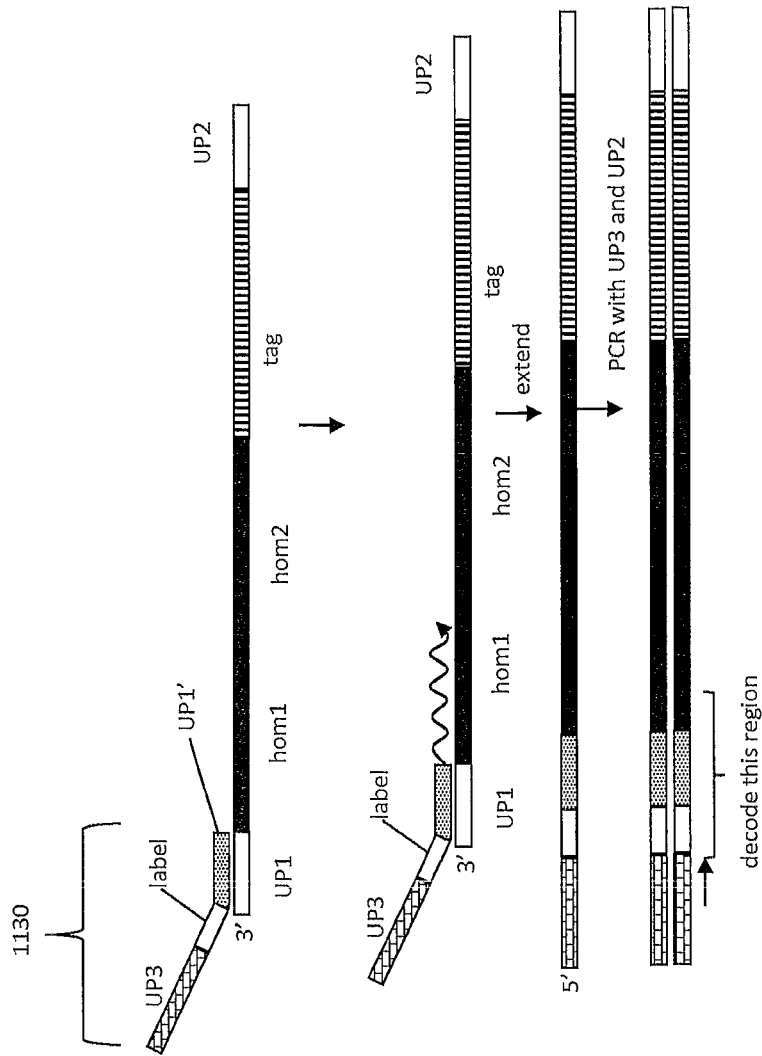
FIG. 9C shows another method for labeling molecular inversion probes with stochastic labels.

In a variation on the method shown in FIG. 9A, stochastically labeled products can be generated from the inverted probes 1128 as shown in FIG. 9B. The inverted probe 1128 is shown 3' to 5' left to right, so that UP1 is at the 3' end and UP2 at the 5' end. A stochastic label can be attached to each individual inverted probe by annealing an oligo 1130 containing (in a 5'-3' orientation) a third universal primer binding site (UP3), a stochastic label, "label" followed by a short sequence 1132 (5-10 bases, for example) that will selectively bind the MIP immediately upstream of the tag sequence (see FIG. 9B). In some aspects the short sequence is an LNA or other modified sequence that has a higher binding affinity so that a shorter region of complementarity can be used. Elongation of this probe will then create a species that contains a stochastic label linked to the MIP tag with a small gap of known sequence (the 1132 region in the figure). It is preferable to make the gap as small as possible so that the stochastic label is close to the MIP tag and requires a shorter read length to sequence. The use of LNAs or CeT's or any other analogue that binds with higher stability facilitates reduction of the length of the gap. The LNA region may be, for example, 5 to 10 bases, but more preferably 4, 5, 6 or 7 bases, Some cross hybridization does not interfere with the assay since the detection step adds an additional layer of specificity and discrimination. The universal binding site UP3 can then be used in conjunction with the other universal primer site UP2 derived from the original MIP to amplify the target using universal primers. Read out may be done using any standard methods as discussed in US Pat. Pub. 20110160078, e.g. sequencing, arrays, etc. In general it is desirable to determine enough of the label-tag to unambiguously identify the label-tag and enough of the probe specific region to unambiguously identify the species of molecular inversion probe and its target species. In another related aspect (shown in FIG. 9C) the label primer with UP3 can be hybridized to the UP1 region and the homology region can be used as a marker for the target.

Probes synthesized using the methods disclosed herein may be used for detection of somatic mutations in heterogeneous mixtures. Somatic mutations occur in any of the somatic cells (not germ cells) of the body and are therefore not passed on to offspring. These alterations are commonly associated with cancer and other diseases. When a cell containing such a mutation continues to divide a patch of tissue may result that has a genotype different from the cells of the rest of the body and different from neighboring cells. Tumor DNA samples can as a result be heterogeneous due to, for example, invasion into stroma, infiltration by immune cells and clonal evolution. The portion of the sample carrying the somatic mutation(s) of interest may be a fraction of the total. MIPs can be designed and synthesized using the methods disclosed herein to specifically detect the somatic mutations. For example the MIP may be allele specific for the somatic mutation so that only in the presence of that mutation with the MIP circularize and generate an amplification product.

EXAMPLES

A pool of 3918 oligos was obtained from LC sciences. The length of the oligos was between 110 and 121 bases in length and have the following structure: 5' AGTCGATGCT CTTCTN$_{20}$GTTC CAACCTTCGA TCTGTGCGGC CGCTCCGAGA ACTAGCATCT TN$_{20}$CACTGCTA TTGACCA-3' (SEQ ID No. 2) where the genomic homology regions are represented by N$_{20}$ and vary between MIPs depending on the target. The nicking sites are between the T and the first N and between the last N and the C. The oligos were provided in a pool after cleavage from the solid support on which they were synthesized. The pooled oligos were amplified by PCR using first preparative primer "oligo_Fwd_V2" 5' ccgtgAGTCGATGCTCTTCT 3' (SEQ ID No. 3) and second preparative prime "oliog_Rev_V2" 5' cagtcTGGTCAATAGCAGTG 3' (SEQ ID No. 4), where the lower case bases represent sequence present in the primers but not complementary to sequence in the precursor MIP. This sequence is added by the primer in the first round of primer extension and will be present in the PCR product. Following PCR the product is subjected to Exo-SAP treatment and Qiagen clean-up. When affinity purification is to be used the primers preferably are biotinylated at their 5' ends. The double stranded product has the sequence 5' CCGTGAGTCGATGCT CTTCTN$_{20}$GTTC CAACCTTCGA TCTGTGCGGC CGCTCCGAGA ACTAGCATCT TN$_{20}$CACTGCTA TTGACCAGACTG 3' (SEQ ID No. 5). The product may be then subjected to TdT treatment in the presence of biotinylated nucleotide so that the 3' ends of the strands are also biotinylated. This may be followed by a clean-up step such as ethanol precipitation.

The pooled product is then nicked with Bts1 at 37° C. and then the enzyme is heat inactivated and BspQ1 is added and incubated at 50° C. followed by heat inactivation. Cleavage by Nt. BspQ1 occurs between the T and the first N. Cleavage by Nb. Bts1 occurs after the final N and before the C.

The products are then heated to 85° C. and incubated with magnetic beads that are at 65° C. coated with streptavidin so that the biotinylated ends of the strands can bind to the beads. Under these conditions the MIPs (117 in FIG. 2) should still be bound to the bottom strand but the shorter primer regions (115 and 119 in FIG. 2) should separate from the full length strand (121 in FIG. 2). The bound products are then subjected to denaturing conditions, e.g. pH 12, so that the MIPs (which are not biotinylated) are released from the beads. The MIPs are then recovered and can be concentrated, for example, by using a CENTRICON column. The resulting pool of MIPs can be used in a MIP assay using analytical primers 5' CACAGATCGAAGGTTGGAAC 3' (SEQ ID No. 6) and 5' GCTCCGAGAACTAGCATCTT 3' (SEQ ID No. 7). Because the MIPs are generated by PCR they do not contain uracil at the cleavage site as previously disclosed. Instead there is a NotI restriction site 5' GCGGCCGC 3' in the central portion of the sequence between the two analytical priming regions. To facilitate cleavage of the closed circular product an oligo complementary to the NotI site and surrounding sequence is hybridized to the single stranded closed circle during the MIP assay to facilitate cleavage of the closed circle prior to amplification. An example of such as oligo is "cNOT29" having the following sequence: 5' AGTTCTCGGACGCCGGCGACAGATCGAAG-3' (SEQ ID No. 8). The last base at the 3' end of the oligo, G in the example provided, is a dideoxy to prevent inadvertent priming off that end in the amplification reaction.

In another example, the pool of probes may be subjected to two rounds of PCR to obtain a larger amount of final product. For example, the amount after the first amplification may be about 375 µg total or enough for about 1600 reactions. A second PCR amplification was performed using the universal primers and resulting in about 375 mg total, enough for 1.6 million samples. The amplification was performed in 2 days. The ligation based production method requires a longer time period of about 10 days.

CONCLUSION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby. All cited references, including patent and non-patent literature, are incorporated herein by reference in their entireties for all purposes and particularly to disclose and describe the methods or materials in connection with which the publications are cited.

We claim:

1. A method for amplifying a plurality of full length probes, the method comprising:
   obtaining a precursor probe comprising from 5' to 3' a first primer complementarity region, a nicking site, a first homology region, a first universal priming site, an analytical cleavage site, a second universal priming site, a second homology region, a second nicking site, and a second primer complementarity region;
   hybridizing a first affinity labelled primer to the second primer complementarity region and extending the first primer to make a first extension product;
   hybridizing a second affinity labelled primer to the 3' end of the first extension product and extending the second primer to make a double stranded extension product;
   amplifying the double stranded extension product by PCR;
   affinity labelling the 3' ends of the amplification product using a terminal transferase;
   cleaving at the first and second nicking sites using first and second nicking enzymes; and
   separating the affinity labelled fragments from the non-affinity labelled fragments, wherein the non-affinity labelled fragments are the full length probes.

2. The method of claim 1, wherein the first and second nicking enzymes are N.BtsI and N.BspQ1.

3. The method of claim 1, wherein the analytical cleavage site comprises an A base and cleavage is by hybridization of an oligonucleotide to the processed probe so that an A:G mismatch is formed at the analytical cleavage site and the mixture is treated with a glycosidase and an AP endonuclease to cleave the processed probe at the analytical cleavage site.

4. The method of claim 1, wherein the affinity label is a member of a binding pair selected from the group consisting of: an antigen/antibody pair, a biotin/avidin pair; an iminobiotin/avidin pair, a protein/protein-interacting pair, a receptor/ligand pair, a nucleic acid/nucleic acid binding protein pair, an antibody/digoxigenin pair, an antibody/fluorescein pair, an antibody/dinitrophenol pair, and a carbohydrates/carbohydrate binding partner pair.

5. The method of claim 1, wherein said first and second nicking sites are both targets for single strand cleavage.

6. The method of claim 1, wherein said separating comprises capture of the affinity labelled fragments on a solid support.

7. A method for preparing a plurality of probes, the method comprising:
   obtaining one or more first precursor probes and one or more second precursor probes wherein the first precursor probes comprises from the 5' end a first common preparative priming site, a first target homology region, a first analytical common priming site, an analytical cleavage site, a second analytical common priming site, and a first tag region and wherein said second precursor probes comprises from the 5' end a second preparative common priming site, a second target homology region, and a second tag region;
   hybridizing the first precursor probes and the second precursor probes whereby the first and second tag regions form a duplex double stranded region; and
   extending the 3' ends of the first precursor probes using the second precursor probes as template and the 3' end of the second precursor probes using the first precursor probes as template to generate one or more double stranded precursor.

8. The method of claim 7, further comprising, cleaving the double stranded precursors to cleave off the first and second preparative priming sites; and separating the plurality of probes by size selection.

9. The method of claim 7, wherein the analytical cleavage site comprises an A base and cleavage is by hybridization of an oligonucleotide to the processed probe so that an A:G mismatch is formed at the analytical cleavage site and the mixture is treated with a glycosidase and an AP endonuclease to cleave the processed probe at the analytical cleavage site.

10. The method of claim 7, further comprising
    amplifying the double stranded precursor using primers to the first and second preparative priming sites; and
    cleaving the amplification product to cleave off the first and second preparative priming sites.

11. The method of claim 7, further comprising separating a full length probe from-the first and second preparative priming sites, said separating being based on size selection.

12. A method for amplifying a plurality of probes to obtain a pool of processed probes, said method comprising:
    (a) obtaining a plurality of precursor probe templates wherein each precursor probe template comprises, in the following order, (i) a first preparative priming region comprising a first preparative cleavage site, (ii) a first target homology region, (iii) a first common analytical priming region, (iii) an analytical cleavage site, (iv) a second common priming region, (v) a tag region, (vi) a second target homology region, and (vii) a second preparative priming region comprising a second preparative cleavage site, wherein there is a precursor probe template for each processed probe in the pool;

wherein the first preparative cleavage site is configured to be a target of a single strand nuclease and the second preparative cleavage site is configured to be target of a double strand nuclease, or wherein the first preparative cleavage site is configured to be a target of a double strand nuclease and the second preparative cleavage site is configured to be target of a single strand nuclease first preparative cleavage site;

(b) hybridizing one or more of the precursor probe templates to its complement, thus forming a double stranded product;

(c) cleaving the product of step (b) with an enzyme that recognizes the second preparative cleavage site; and, (d) cleaving the product at the first and second cleavage sites to provide the plurality of processed probes.

13. The method of claim 12, wherein said hybridizing is of precursor probe templates amplified using a first preparative primer for the first preparative priming region and a second preparative primer for the second preparative priming region, wherein the first preparative primer is labelled.

14. The method of claim 13, wherein the first preparative primer is labelled with a label selected from the group consisting of biotin, digoxigenin, and fluorescein.

15. The method of claim 14, wherein the labelled strands are separated from the non-labelled strands by mixing the reaction with beads coated with an affinity reagent that binds to the label.

16. The method of claim 15, wherein the affinity reagent is an antibody to biotin, digoxigenin or fluorescein.

17. The method of claim 12, wherein the analytical cleavage site comprises an A base and cleavage is by hybridization of an oligonucleotide to the processed probe so that an A:G mismatch is formed at the analytical cleavage site and the mixture is treated with a glycosidase and an AP endonuclease to cleave the processed probe at the analytical cleavage site.

18. The method of claim 13, wherein said recovering comprises binding the labelled first preparative primer to a binding pair partner on a solid support to separate the labelled common priming region from the processed probes.

* * * * *

SEQUENCE LISTING

```
<160> NUMBER OF SEQ ID NOS: 9

<210> SEQ ID NO 1
<211> LENGTH: 115
<212> TYPE: DNA
<213> ORGANISM: Artificial
<220> FEATURE:
<223> OTHER INFORMATION: Synthetic

<400> SEQUENCE: 1
aggaccagct cttctaagtc gtgagcttgc agcttcttca gcttcccgat tacggcggcc      60
gcacgatccg acggtagtgt gcaggctgtc attactccac cactgcgtga actga          115

<210> SEQ ID NO 2
<211> LENGTH: 96
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (16)..(35)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 2
agtcgatgct cttctnnnnn nnnnnnnnnn nnnnngttcc aaccttcgat ctgtgcggcc      60
gctccgagaa ctagcatctt ncactgctat tgacca                               96

<210> SEQ ID NO 3
<211> LENGTH: 20
<212> TYPE: DNA
<213> ORGANISM: Artificial
```

```
<220> FEATURE:
<223> OTHER INFORMATION: Synthetic

<400> SEQUENCE: 3
ccgtgagtcg atgctcttct                                          20

<210> SEQ ID NO 4
<211> LENGTH: 20
<212> TYPE: DNA
<213> ORGANISM: Artificial
<220> FEATURE:
<223> OTHER INFORMATION: Synthetic

<400> SEQUENCE: 4
cagtctggtc aatagcagtg                                          20

<210> SEQ ID NO 5
<211> LENGTH: 125
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (21)..(40)
<223> OTHER INFORMATION: n is a, c, g, or t
<220> FEATURE:
<221> NAME/KEY: misc_feature
<222> LOCATION: (86)..(105)
<223> OTHER INFORMATION: n is a, c, g, or t

<400> SEQUENCE: 5
ccgtgagtcg atgctcttct nnnnnnnnnn nnnnnnnnnn gttccaacct tcgatctgtg    60
cggccgctcc gagaactagc atcttnnnnn nnnnnnnnnn nnnnncactg ctattgacca   120
gactg                                                              125

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
cacagatcga aggttggaac                                          20

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
gctccgagaa ctagcatctt                                          20

<210> SEQ ID NO 8
<211> LENGTH: 29
<212> TYPE: DNA
<213> ORGANISM: Artificial
<220> FEATURE:
<223> OTHER INFORMATION: Synthetic

<400> SEQUENCE: 8
agttctcgga cgccggcgac agatcgaag                                29
```

```
<210> SEQ ID NO 9
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(22)
<223> OTHER INFORMATION: n is a, c, g, or t

<400> SEQUENCE: 9
gcagtgnnnn nnnnnnnnnn nngaagagc                                  29
```